US009556469B2

(12) United States Patent
Marcoux et al.

(10) Patent No.: US 9,556,469 B2
(45) Date of Patent: Jan. 31, 2017

(54) METHOD FOR CLASSIFYING THE PRESENCE OR ABSENCE OF A MICROORGANISM IN A BIOLOGICAL MEDIUM

(75) Inventors: Pierre Marcoux, Saint Egreve (FR); Mathieu Dupoy, Grenoble (FR); Laure-Hélène Guillemot, Paris (FR); Thu-Hoa Tran-Thi, Montrouge (FR)

(73) Assignees: Commissariat a l'Energie Atomique et aux Energies Alternatives, Paris (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 14/127,939

(22) PCT Filed: Jun. 27, 2012

(86) PCT No.: PCT/IB2012/053249
§ 371 (c)(1),
(2), (4) Date: Feb. 24, 2014

(87) PCT Pub. No.: WO2013/001465
PCT Pub. Date: Jan. 3, 2013

(65) Prior Publication Data
US 2014/0162301 A1 Jun. 12, 2014

(30) Foreign Application Priority Data
Jun. 27, 2011 (FR) ...................... 11 55690

(51) Int. Cl.
*C12Q 1/04* (2006.01)
*G01N 1/22* (2006.01)
*G01N 21/17* (2006.01)
*C12Q 1/18* (2006.01)

(52) U.S. Cl.
CPC . *C12Q 1/18* (2013.01); *C12Q 1/04* (2013.01); *C12Q 2334/10* (2013.01); *C12Q 2334/30* (2013.01)

(58) Field of Classification Search
None
See application file for complete search history.

(56) References Cited

U.S. PATENT DOCUMENTS

| | | | |
|---|---|---|---|
| 4,945,060 A | 7/1990 | Turner et al. | 435/288.7 |
| 6,022,748 A * | 2/2000 | Charych | B82Y 30/00 436/527 |
| 2003/0166298 A1 | 9/2003 | Suslick et al. | 436/169 |
| 2005/0171449 A1 | 8/2005 | Suslick et al. | 600/532 |
| 2006/0223052 A1* | 10/2006 | MacDonald | G01N 33/523 435/5 |
| 2008/0199904 A1 | 8/2008 | Suslick et al. | 435/34 |
| 2010/0255530 A1* | 10/2010 | Monget | C12Q 1/045 435/38 |
| 2010/0273209 A1 | 10/2010 | Eden et al. | 435/39 |
| 2010/0291617 A1* | 11/2010 | Trevejo | C12Q 1/04 435/34 |

FOREIGN PATENT DOCUMENTS

| | | |
|---|---|---|
| CN | 101070520 | 11/2007 |
| CN | 101395278 | 3/2009 |
| CN | 101948902 | 1/2011 |
| WO | WO 94/04705 | 3/1994 |
| WO | WO 02/38724 | 5/2002 |
| WO | WO 2006/107370 | 10/2006 |
| WO | WO 2007/031657 | 3/2007 |
| WO | WO 2009/091402 | 7/2009 |
| WO | WO 2010/004225 | 1/2010 |
| WO | WO 2010/028057 | 3/2010 |

OTHER PUBLICATIONS

PubChem. 2-Nitrophenol. Datasheet [online]. NCBI, NIH. Create date: Sep. 16, 2004. [retrieved on Sep. 8, 2015]. Copyright NCBI.NLM.NIH. Bethesda, MD. Retrieved from the Internet: <URL: http://pubchem.ncbi.nlm.nih.gov/—/6947>. p. 1.*
Dickert, F.L. 2002. Sensor materials—detecting molecules, mixtures, and microorganisms. Materials Research Society Symposium Proceedings 723: M2.1.1-M2.1.10; specif. pp. M2.1.1, M2.1.2.*
Wang, X. et al. 2005. Direct synthesis and catalytic applications of ordered large pore aminopropyl-functionalized SBA-15 mesoporous materials. Journal of Physical Chemistry 109: 1763-1769. specif. pp. 1763, 1765.*
McClellan, R.O. Test Agent Generation. In: Biological Concepts and Techniques in Toxicology. Copyright 2006. Taylor & Francis Group, LLC. Ed.: Jim E. Riviere. New York, NY, p. 324.*
PubChem. Tetraethoxysilane. Datasheet [online]. NCBI, NIH. Deposit date: Nov. 13, 2014. [retrieved on Sep. 8, 2015]. Copyright NCBI.NLM.NIH. Bethesda, MD. Retrieved from the Internet: <URL: http://pubchem.ncbi.nlm.nih.gov/substance/223365854>. pp. 1, 4.*
Armon et al., "Sol-gel applications in environmental biotechnology", *Journal of Biotechnology*, 51(3):279-285, 1996.
International Search Report and Written Opinion issued in PCT Application No. PCT/IB2012/053249, mailed Jan. 31, 2013.
Search Report issued in French Patent Application No. FR1155690, mailed Mar. 8, 2012.
Loiseau et al., "A fluoroponytails containing organogelator: gelation of perfluorotributylamine and isopropopanol", 2002, Tetrahedron, vol. 58, pp. 4049-4052.

* cited by examiner

*Primary Examiner* — Renee Claytor
*Assistant Examiner* — Sharon M Papciak
(74) *Attorney, Agent, or Firm* — Norton Rose Fulbright US LLP

(57) ABSTRACT

Porous sol-gel material essentially consisting of units of one or more first polyalkoxysilanes chosen from the following compounds: (chloromethyl)triethoxysilane; 1,3-dimethyltetramethoxydisiloxane; ethyltrimethoxysilane; triethoxy(ethyl)silane; triethoxymethylsilane; triethoxy(vinyl)silane; trimethoxymethylsilane; trimethoxy(vinyl)silane; tetraethoxysilane or tetramethoxysilane (TMOS) and of units of one or more second polyalkoxysilanes chosen from the following compounds: (N-(3-(trimethoxysilyl)propyl)ethylenediamine; 3-aminopropyltriethoxysilane (APTES) and 3-aminopropyltrimethoxysilane, in a first polyalkoxysilane/second polyalkoxysilane molar ratio of 1/0.01 to 1/1, optionally comprising a probe molecule, method of preparation and applications in the trapping of monocyclic aromatic hydrocarbons and other pollutants or in their detection.

22 Claims, 6 Drawing Sheets

Figure 1:
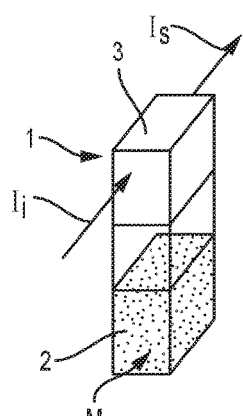

METHOD FOR CLASSIFYING THE PRESENCE OR ABSENCE OF A MICROORGANISM IN A BIOLOGICAL MEDIUM

CROSS-REFERENCE TO RELATED APPLICATIONS

This application is a national phase application under 35 U.S.C. §371 of International Application No. PCT/IB2012/053249 filed 27 Jun. 2012, which claims priority to French Patent Application No. 1155690 filed 27 Jun. 2011. The entire contents of each of the above-referenced disclosures is specifically incorporated herein by reference without disclaimer.

The present invention relates to a method for determining the presence of at least one microorganism, generally pathogenic, in particular in a biological sample, preferably physiological, and most preferably blood.

Blood culture is the culture of blood in or on a nutrient medium to produce bacterial growth. The objective consists in amplifying the concentration of a pathogenic species by giving it conditions favorable for growth, so as to detect it in a patient presenting sepsis.

Blood culture is currently the only method of detection for blood-borne infections and for microbiology laboratories it represents a frequent test, of the order of a third of activity.

Fundamentally, it is a simple detection test. The manual, conventional technique consists in incubating flasks containing the biological sample to be analyzed in an oven between 35 and 37° C., and to observe each flask once a day for at least 10 days to detect bacterial proliferation in the form of turbidity.

Technological advances in the last thirty years in the field of blood culture have led to automation of analyses, and a significant reduction in detection and identification time.

Process automation generally consists in detecting a metabolite, i.e. a chemical compound that comes from bacterial metabolism, a sort of waste inherent to the microbial growth. Many of these metabolites, also called VOC (Volatile Organic Compound) below, are gaseous or volatile. Accordingly, some automated systems exploit $CO_2$ formation, as this proves to be the most generic metabolite emitted by growing microorganisms. Conversely, other automated systems may show microbial growth by detecting consumption of a nutrient, $O_2$ consumption for example.

For $CO_2$ detection, several technologies have been used that are distinguished in particular by the analytical method used to characterize the $CO_2$.

Developed from the 1970s, a technology called continuous BACTEC, with non-invasive detection, is based on radiometric respirometry. More specifically, it relies on metabolizing $^{14}C$-labeled enzymatic substrates so that emission of a volatile metabolite can be detected by counting beta particles at 156 keV.

According to one of the variants of the invention, called BACTEC 9240, the base of a flask containing the biological sample to be characterized contains a gas-permeable polymer, generally a silicone polymer, and includes a pH-sensitive fluorophore probe molecule. When the $CO_2$ diffuses from the liquid to the hydrated substance, it forms carbonic acid $H_2CO_3$, which acidifies the polymer and increases the fluorescence emitted by the fluorophore (EP 682 252).

Another technology, called BacT/ALERT, very similar to BACTEC 9240, uses a gas-permeable polymer also including a pH-sensitive probe molecule, but embodied, in that case, by a chromophore probe. When the $CO_2$ diffuses from the liquid to the hydrated substance, it forms carbonic acid $H_2CO_3$, which acidifies the polymer, making it less opaque and more reflective.

In the 1990s, a continuous monitoring blood culture automated system was proposed (VITAL), also based on using fluorescent probe molecules with a view to characterizing them using optical transduction. However the probes are not arranged at the base of the flask, but in solution in the culture medium. Their fluorescence is inhibited by protons and reducing molecules. Consequently, bacterial growth is shown by reduced fluorescence.

Another type of technology, not specific to the detection of a particular VOC, and distributed under the name Versa TREK, relies on manometric detection. All of the gaseous metabolites generated are detected, including $CO_2$, the main metabolite. Each flask is sealed closed and equipped with a detector that continuously monitors the gas pressure above the culture medium.

Devices have also been proposed that allow simultaneous detection of several volatile metabolites in the gas phase. Such a device comprises several detectors that are respectively specific to a particular VOC (or to a specific family of VOC), and detection uses direct optical transduction. A substrate is soaked with an "indicator", i.e. a molecule that can undergo a color change in the presence of the VOC identified as relevant (J. G. McDonald et al.: WO 2006/107370).

An exploratory phase of analyzing VOCs emitted by a given species subsequently allows characterization in a medium for analyzing the presence of the same VOCs. The VOCs emitted by culturing this species are concentrated by adsorption on a SPME cartridge. The compounds are then desorbed and analyzed by GC-MS coupling. Gas phase chromatography (GC) can quantify the various compounds and mass spectrometry (MS) is profitably used to identify them.

Another technology proposes the use of a wide variety of probes that can react with VOCs by non-covalent interactions (Van der Waals interactions, hydrogen bonds, n-n complexes, charge transfer, acid-base interactions in the sense of Brönsted or Lewis). A target VOC will interact with one or more target(s), which will cause one or more color changes (K. S. Suslick et al.: US 2003/0166298). The color change map for the matrix of probes constitutes the multi-parameter response of the detector to the presence of the VOC.

This principle of colorimetry identification is in particular taken advantage of in the domain of non-invasive in vivo diagnostics. More precisely it is used to explore the presence of a pathogen in the stomach (*Helicobacter pylori*) by analyzing the subject's breath. *H. pylori* is characterized by high urease production, an enzyme that degrades urea into ammonia and $CO_2$. A urea lozenge is given to the patient, whose breath is then put in contact with a matrix of colorimetric probes.

Regarding detection of mycobacteria, the automated systems are based on the same technologies as those of blood culture automated systems. The objective is the same, i.e. to detect microbial growth in a liquid culture medium. The only difference lies in the composition of the culture media.

Indeed, as is obvious from that which precedes, all the technologies discussed hereinabove rely essentially on the characterization of a metabolite inherent to microbial growth and generally not specific to a microorganism, such as the metabolite $CO_2$. The formation of this metabolite is generally attested via its interaction with a fluorophore probe sensitive to pH or a chromophore probe arranged for this purpose in the enclosure containing the medium to be analyzed.

It appears that the previously cited detection methods are not completely satisfactory.

Accordingly, regarding $CO_2$ detection by the BioLumix technique (US 2010/0273209 A1) for example, there is a high background for $CO_2$, in particular residual $CO_2$ in air ($\approx$390 ppm), which affects the results.

In the BacT/ALERT (J. Turner et al., U.S. Pat. No. 4,945,060) or BioLumix (US 2010/0273209 A1) technologies, the probes used are pH probes. These probes are not therefore specific. Any other volatile metabolite having acid-base properties (proton donors or acceptors, such as ammonia or indole for example) will, if present, affect the results. In buffered media, such as blood for example, carbonic acid detection is more difficult.

Moreover, these technologies use substrates that develop low mass surface area (in $m^2/g$). That is, these are heterogeneous reactions. The probe is in fact on the surface of a solid, and the target metabolite is in a fluid (liquid or gas) in contact with the detector. Therefore, to improve the detection kinetics, it seems important to increase the contact surface area between the solid phase and the fluid to a maximum.

What is more, in the BacT/ALERT technology for example, the diffusion distance that the volatile metabolite must sometimes cover is high (U.S. Pat. No. 4,945,060).

Finally, these technologies do not allow the parasitic effect to be released, if necessary, in particular in terms of fluorescence, color or absorbance, that can be generated in parallel by compounds that are appended and therefore distinct from the microorganism to be characterized and that would also be present in the medium.

Consequently, the present invention aims to propose a new detection method that can at least partially supplement the previously cited drawbacks.

Accordingly, according to one of its features, the present invention relates to a method for determining the presence or absence of at least one microorganism in a biological medium, said method comprising at least the steps consisting in:
1) providing an enclosure containing:
  a liquid or semi-solid phase formed in whole or in part of said biological medium capable of containing at least one living form of said microorganism, nutritional elements necessary for proliferation of said microorganism, and an enzymatic substrate that is specific to said microorganism and that can be metabolized into at least one VOC volatile metabolite, and
  a gas phase adjacent to said liquid or semi-solid phase,
2) exposing at least said liquid or semi-solid phase to conditions that are favorable for said microorganism to metabolize said enzymatic substrate into at least one molecule of said VOC metabolite, and
3) determining, by optical transduction, the presence or absence of said VOC metabolite, an indicator of the presence of said microorganism,
characterized in that said VOC metabolite, if formed in step 2), interacts with a nanoporous matrix, and in that the detection, by optical transduction, of a change in the optical properties of said matrix indicates an interaction of said matrix with said metabolite.

More particularly, the present invention relates to a method for determining the presence or absence of at least one microorganism in a biological medium, said method comprising at least the steps of:
1) providing an enclosure containing:
  a liquid or semi-solid phase formed in whole or part of said biological medium capable of containing at least one living form of said microorganism, nutritional elements necessary for proliferation of said microorganism, and an enzymatic substrate that is specific to said microorganism and that can be metabolized into at least one VOC volatile metabolite, and
  a gas phase adjacent to said liquid or semi-solid phase,
2) exposing at least said liquid or semi-solid phase to conditions that are favorable for said microorganism to metabolize said enzymatic substrate into at least one molecule of said VOC metabolite, and
3) determining, by optical transduction, the presence or absence of said VOC metabolite, an indicator of the presence of said microorganism, characterized in that:
  said VOC metabolite, if formed in step 2), interacts with a nanoporous matrix, said matrix being implemented in a form that is separate from said enzymatic substrate, and
  the detection by optical transduction of a change in the optical properties of said matrix indicates that said matrix interacts with said metabolite.

In this preferred embodiment, the matrix is arranged in such a manner as to have no physical contact with the enzymatic substrate(s) also used in the method according to the invention. This absence of any contact between the sensor(s) present in the matrix and the analyte, advantageously prevents any phenomenon of contamination, in particular pollution of these sensor(s) by the analyte.

This lack of contact between the two types of entities may be in particular obtained by arranging the matrix in the gas phase. However, other separation methods, in particular in the variant where the matrix is submerged, or in contact with the liquid or semi-solid phase containing the enzymatic substrate, may also be considered. Their development clearly falls within the skills of the person skilled in the art.

As is obvious from that which precedes, the method according to the invention relies on the detection of one or more microorganisms, in particular one or more bacteria, in a sample that is generally biological via the characterization, in the gas phase or the liquid phase, of one of their enzymatic routes.

More precisely, to detect one or more microorganism(s), the enzymes of the microorganism species presumed to be present in the medium to be analyzed, lead to degradation of the metabolizable enzymatic substrate considered according to the invention in at least one volatile metabolite called VOC. The gaseous molecules of this VOC metabolite are captured and concentrated in a nanoporous matrix with high specific surface area and it is the change in optical properties in the nanoporous matrix, caused by adsorption and accumulation of the VOC metabolite in its pores, which will allow the determination of the presence or absence of the microorganism that is the subject of detection in the biological medium to be analyzed.

According to a preferred embodiment, said metabolite has intrinsic optical properties.

As detailed below, this metabolite additionally has a Henry constant in said liquid or semi-solid phase that prefers a gaseous state.

This metabolite is advantageously specific or what is called exogenous.

The term "exogenous VOC metabolite" is understood to mean a metabolite generated unnaturally during the microbial development of the microorganism being considered, or even distinct from natural metabolites generated during microbial growth such as for example $CO_2$. In other words, this VOC metabolite cannot be generated by microorganisms other than those that are the subject of detection.

Thus, according to a preferred embodiment, said VOC metabolite considered according to the invention is distinct from natural metabolites generated during microbial growth.

Advantageously, the VOC metabolite considered according to the invention is a metabolite specific to the metabolization of the associated enzymatic substrate and is therefore representative of an enzymatic route selective for the microorganism that is the subject of detection.

The nanoporous matrix considered according to the invention may be arranged in the gas phase or the liquid phase in said enclosure.

In a preferred variant of the invention, detection by optical transduction may be advantageously conducted in said matrix that is arranged in the gas phase.

This embodiment allows the parasitic effect to be released, in particular in terms of fluorescence, color or absorbance, that can be generated in parallel by compounds that are appended and therefore distinct from the microorganism to be characterized and that would be also present in the medium.

In such an embodiment, the matrix located in the gas phase may be for example arranged in the headspace of a blood culture flask.

According to a preferred embodiment, the nanoporous matrix comprises a molecule, called a probe molecule, that can interact specifically with the VOC that is the subject of detection. This specific interaction causes the formation of a product whose optical properties can be detected. This embodiment generally delivers better detection specificity.

"Biological medium" is understood to mean any sample of liquid, semi-solid, or solid substance that can be suitable for survival, or even growth and/or proliferation, of at least one microorganism.

As non-limiting examples, a biological medium may be a medium dedicated to a food, cosmetic or pharmaceutical application and more preferably be a physiological medium.

More particularly, a biological medium may in particular be a biological sample such as serum, urine, saliva or sperm, a highly colored (colored drinks, blood) or diffusing (food matrices) or intrinsically fluorescent (some culture-specific media, such as Löwenstein-Jensen medium, or some food matrices such as the liver) sample.

Preferably, the biological medium is formed in whole or part of a food sample or of a physiological sample.

A microorganism considered by the invention may be embodied by a species of bacteria, yeast, mold, protozoa, or even a virus cultivated in a host cell. Preferably, a microorganism of the invention is embodied by a species of bacterium, in particular one that can be pathogenic for mammals such as humans.

The liquid or semi-solid phase considered as a whole represents the culture medium for the microorganism to be detected.

The term "semi-solid" is understood to in particular designate culture media called agar.

As detailed below, the VOC metabolite may be detected by absorbance and/or fluorescence.

According to a preferred embodiment, the nanoporous matrix is used as a waveguide and is for example shaped like a long cylinder. With a higher index than air or water, this waveguide may be submerged in the fluid phase (liquid or gas) where the target metabolite is found.

A waveguide having long cylindrical shape may reduce the distance that the target metabolite must cover before reaching the light beam.

The method considered according to the invention is advantageous in several ways.

First, the fact that the VOC volatile metabolite released is adsorbed in the gas phase or in the liquid phase in a porous, preferably transparent, matrix and advantageously with high specific surface area, i.e. at least equal to 300 $m^2/g$ and preferably between 400 and 900 $m^2/g$, increases the detection kinetics significantly compared to conventional technologies.

The method according to the invention is further compatible with characterization of microorganisms cultivated in all types of media, i.e. whether they are liquid or not, colored or not, diffusing or not, such as for example blood cultures (high hemoglobin absorbance in blood, to which the light diffused and absorbed by the particles inhibiting the antibiotics must be added), and some food matrices (food additives with intrinsic fluorescence or diffusing media) or some culture media for microorganisms.

In all these media, the use of conventional chromogenic or fluorogenic enzymatic substrates is ordinarily disturbed by their intrinsic optical properties. For example, the substrate p-nitrophenyl-β-D-galactopyranoside (pNPG) has been known for a long time for showing the presence of bacteria, by monitoring the absorbance of the associated liquid phase at 301 nm or 418 nm. Unfortunately, analytical technologies relying on the use of such a chromogenic substrate cannot be applied in a diffusing and/or absorbent culture medium.

This advantage is also particularly appreciable for mycobacteria detection. Indeed, the culture media used classically to characterize these microorganisms must include inhibitors in the interest of preventing other microorganisms from developing there due to sample contamination, to the detriment of mycobacteria that are the subject of detection. So essentially, these inhibitors are both colored and fluorescent, which hinders using chromogenic or fluorogenic substrates to demonstrate the presence of any mycobacteria that may potentially be in the culture.

Certainly, the principle of detecting a microorganism via the characterization of a VOC featuring a metabolism product inherent to its growth and proliferation, in particular the case of $CO_2$, by optical transduction is known; this principle is in particular described in WO 2006/107370, US 2005/0171449, WO 2010/028057, US 2003/0166298 and US 2008/0199904. However, all of the existing technologies generally require the use of dedicated probes to interact with a VOC formed during microbial development, generally $CO_2$, and are not therefore specific to a particular enzymatic route and representative of a specific microorganism.

The technologies of the prior art do not therefore use substrates specific to an enzymatic route.

Moreover, when these probes are supported, the substances considered in these conventional technologies do not allow access to satisfactory detection sensitivity, in light of their low specific surface area.

By contrast, the invention has the advantage of using a specific interaction between the nanoporous matrix, or the probe molecule that it contains, and a VOC, the VOC being representative of an enzymatic route specific to the microorganism that is the subject of detection. Accordingly, to characterize a specific enzyme, a substrate specific to an enzymatic route can be determined, so that the interaction between the enzyme and the substrate generates an easily detectable predetermined VOC.

Because this VOC is different from natural metabolites, it is possible to reduce the background noise, i.e. the signal in the absence of the microorganism. The consequence of this is a drop in detection limit, and reduced risk of false positives.

According to another object the present invention relates to the use of a method of the invention to detect the presence of microorganism(s) in a biological medium and preferably in a physiological medium.

According to a further object, the present invention relates to the use of a method of the invention to establish the phenotype of a microorganism.

According to a further object, the present invention relates to the use of a method of the invention to conduct an antibiogram test i.e. to test the efficacy of an antibiotic (AST: Antibiotic Susceptibility Testing). The subject is then to detect bacterial growth in the presence of a known concentration of antibiotic.

According to a further object, the present invention relates to the use of a method of the invention to conduct a microorganism count by the most-probable number method (MPN). Advantageously it enables determination of whether, in an elementary volume, bacteria exists. To count the bacteria, the analytical volume is divided into several sub-volumes to detect whether or not there is bacterial growth in each of the sub-volumes. The results are then used to count a number of bacteria.

According to a further object, the present invention relates to the use of a method of the invention to test, using enzymatic characterization, certain antibiotic resistances. For example, VanX enzymatic activity is characteristic of a high level of resistance to the vancomycin. It may be tested with substrates that, once metabolized, will release the thiophenol, or 4-nitroaniline.

According to a further object, the present invention relates to the use of a method of the invention to conduct screening of vancomycin-resistent strains, shown by the evidence of VanX.

VOC Volatile Metabolite

As is obvious from that which precedes, this volatile molecule comes from the enzymatic degradation of an enzymatic substrate specific to the microorganism to be detected according to the invention. Accordingly, a VOC volatile metabolite considered by the invention may constitute, at least partially, an enzymatic substrate specific to the microorganism to be detected.

It is generated in the microorganism itself and crosses the cell wall to be found in the liquid or semi-solid phase.

This VOC can, in the scope of the present invention, only be generated from the specific enzymatic substrate required according to the invention.

For this purpose, it is distinct from VOCs or even natural volatile metabolites that can be generated during the microbial growth.

Accordingly, it is advantageously other than $CO_2$.

In the scope of the present invention, the VOC volatile metabolite being considered has the highest possible Henry's constant, $H_{cc}$, i.e. preferring a gaseous state compared to a liquid or semi-solid state.

More precisely, for a volatile compound Henry's law determines the partition coefficient at the equilibrium between a dilute aqueous solution and a gas phase. If $C_{i,L}$ is the volume concentration of the volatile compound i in the aqueous phase (in $g/m^3$ or in $mol/m^3$) and $C_{i,G}$ its volume concentration in the gas phase (in the same unit: $g/m^3$ or $mol/m^3$), then Henry's constant is the following size without dimension:

$$H_{CC} = \frac{C_{i,G}}{C_{i,L}}$$

This law expresses that, for a given volatile compound at a given temperature and pressure, at equilibrium the same partition coefficient is always found between the two phases. It is important to note that there are many manners of expressing this law, according to the definition that is used for Henry's constant.

VOC metabolites with high Henry's constant $H_{cc}$ have values of $5 \cdot 10^{-2}$ and higher, ranging up to about $10^2$, whereas average values are around $5 \cdot 10^{-4}$ to $5 \cdot 10^{-2}$ and low values are around $10^{-5}$.

As specified hereinabove, Henry's constant $H_{cc}$ can vary as a function of certain physical parameters in the liquid or semi-solid phase considered in parallel, such as pressure, salinity, temperature, etc.

Accordingly, in the case of a liquid culture medium, it is within the reach of the person of skill in the art to adjust certain physical parameters of this medium to generate a maximum of gaseous compound from the solute. This feature is described in more detail below.

Alternatively, in the case of a solid or semi-solid agar-type culture medium, the pressure or temperature properties of the gas phase can be influenced to favor microbial growth for a certain period (3-5 h) to accumulate the specific target VOC metabolite in the liquid phase then to stop the microbial growth.

Accordingly, the volatilization of the metabolite is favored by increasing the temperature and/or reducing the pressure.

The target VOC metabolite concentration in the liquid phase then increases up to reaching a plateau. Once this plateau is reached, which limits the detection kinetics, it is the transfer of the target metabolite from one phase to the other, and no longer microbial growth.

In the variant of the invention where the nanoporous matrix is directly submerged in the liquid phase (which is the phase where there will always be the most target VOC metabolite), this approach may not be considered.

What is more, the interactions between the solubility in aqueous medium and the vapor pressure condition the volatilization of a given product from the aqueous solution.

For example, a VOC volatile metabolite soluble in water but having high vapor pressure volatilizes quickly.

Preferably, a VOC volatile metabolite soluble in water such as required according to the invention presents, at T=20° C., a vapor pressure comprised between $10^{-4}$ and $10^2$ mbar, preferably a vapor pressure greater than $10^{-3}$ mbar.

According to an advantageous variant, this metabolite may itself have optical properties (absorbance, fluorescence, luminescence) meaning that it can be detected by optical transduction.

In the case of absorbance detection, the associated nanoporous matrix is transparent or poorly absorbent in the detection area, and preferably does not absorb in broad bands of the UV-visible spectrum. Adsorption and accumulation of an absorbent VOC metabolite in the pores of the matrix will translate as increased absorbance.

In the case of fluorescence detection, the associated nanoporous matrix is void of intrinsic fluorescence or has low fluorescence. Adsorption and accumulation of a fluorescent VOC metabolite in the pores of the matrix will translate as increased fluorescence in the matrix.

According to an embodiment, a VOC metabolite suitable for the invention may be chosen from phenol derivatives, such as nitrophenol, cyanophenol, cyanonitrophenol, acetylphenol, propionylphenol derivatives, thiophenol derivatives, naphthol derivatives, aniline derivatives, such as nitroaniline derivatives, or naphthylamine derivatives.

As a non-limiting illustration of VOC metabolites that are particularly suitable for the invention thiophenol, nitronaphthol, p-nitroaniline or 2-naphthylamine may in particular be cited.

According to an advantageous variant of the invention, the VOC volatile metabolite formed may be a photoacid or a photobase.

A certain number of molecules have acid-base properties that differ in the ground state and the excited state (after absorption of a photon). Accordingly, the excitation may trigger a proton transfer. For example, an OH substituent on a naphthol, may be excited so that the pKa* of this group in the excited state is much lower than the pKa in the ground state. Fluorescence can also be observed with a species such as 2-naphthol for example, because the photoinduced proton transfer allows it to be deprotonated into a fluorescent species, here 2-naphtholate. Similarly, a VOC volatile metabolite such as paranitrophenol (pNP) absorbs in the visible, in particular in its basic form.

Of course, the chemical nature of the metabolite is closely linked to the detection method selected when the change in optical properties observed in the matrix is directly caused by its presence.

If absorbance detection is considered, the VOC formed may be more particularly chosen from the following molecules:
  p-cyanophenol whose molar extinction coefficient is $(2.1\pm0.2)\cdot10^4$ $M^{-1}\cdot cm^{-1}$ at 245.8 nm for the neutral form and $(2.6\pm0.2)\cdot10^4$ $M^{-1}\cdot cm^{-1}$ for the anionic form;
  p-nitrophenol (pNP) whose molar extinction coefficient s is $(1.8\pm0.1)\cdot10^4$ $M^{-1}\cdot cm^{-1}$ for the anionic form at 400 nm and 8300 $M^{-1}\cdot cm^{-1}$ for the neutral form at 317 nm (the o-nitrophenol isomer absorbs less ($\epsilon=3\cdot10^3$ $M^{-1}\cdot cm^{-1}$ at 414 nm));
  m-cyano-p-nitrophenol (mCNpNP) whose molar extinction coefficient $\epsilon$ is $1.7\cdot10^4$ $M^{-1}\cdot cm^{-1}$ at 405 nm;
  2,6-dichloro-4-nitrophenol (DCNP);
  2,6-dichloro-4-acetylphenol whose maximum absorption is at pH 5.4 and at 334.2 nm with $\epsilon=2.1\cdot10^4$ $M^{-1}\cdot cm^{-1}$ at 340 nm; or
  naphthol derivatives such as α-naphthol or β-naphthol (1-naphthol or 2-naphthol), α-naphthylamine or β-naphthylamine (1-naphthylamine or 2-naphthylamine).

To allow absorbance detection, these derivatives may require the presence of a probe molecule in the matrix. For example, β-naphthylamine may interact with dimethylaminocinnamaldehyde to form a colored compound. β-Naphthol may interact with the molecule whose common name is "Fast Blue BB", to form a colored compound. These naphthol derivatives may also present useable fluorescence properties.

Thiophenol, 2,6-dichloro-4-propionylphenol, 2,6-difluoro-4-acetylphenol, 2,6-dibromo-4-acetylphenol, and 4-nitroaniline (p-nitroaniline) may also be considered.

For naphthol derivatives having lower absorbance, it can be interesting to make these derivatives interact in the matrix with a reagent such as Fast Blue BB or p-dimethylaminocinnamaldehyde to increase their absorbance. The fact of being able to accomplish this determination directly in a gas phase is particularly advantageous given that these reagents are toxic to microorganisms. The viability of the microorganisms present in the liquid or semi-solid phase is then not affected.

If absorbance detection is considered, the VOC volatile metabolite formed may be more particularly chosen from the following molecules:
p-nitrophenol (4-nitrophenol):

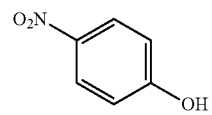

m-cyano-p-nitrophenol (3-cyano-4-nitrophenol):

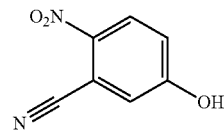

2,6-dichloro-4-acetylphenol:

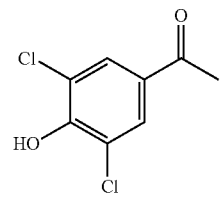

2,6-dichloro-4-propionylphenol:

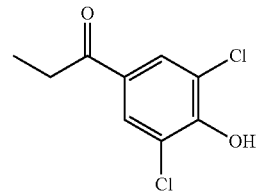

2,6-difluoro-4-acetylphenol:

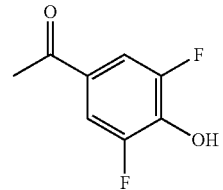

2,6-dibromo-4-acetylphenol:

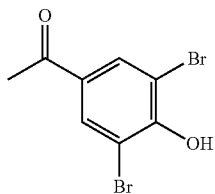

4-nitroaniline (p-nitroaniline):

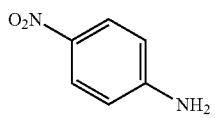

β-naphthylamine (2-naphthylamine):

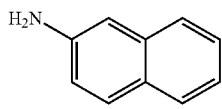

If fluorescence detection is considered, the VOC volatile metabolite formed may be more particularly chosen from the following molecules:

umbelliferone (7-hydroxycoumarin):

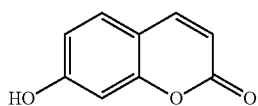

naphthazarin:

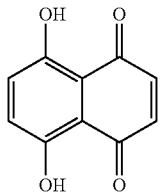

4-trifluoromethylumbelliferone (7-hydroxy-4-trifluoromethylcoumarin):

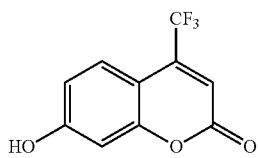

4-methylumbelliferone (4-MU):

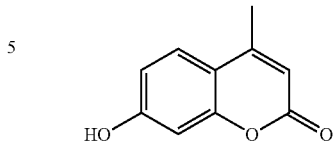

and from the following photoacids and photobases:

o-cyanophenol:

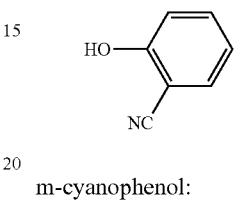

m-cyanophenol:

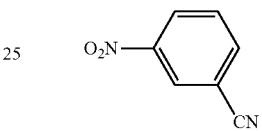

1-naphthol:

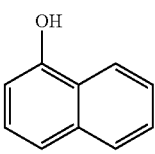 [SMILES: Oc1cccc2ccccc12]

2-naphthol:

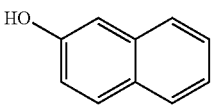

6-cyano-2-naphthol:

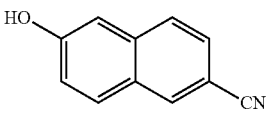 [SMILES: N#Cc1ccc2cc(O)ccc2c1]

6-hydroxyquinoline-N-oxide:

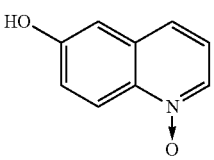 [SMILES: [O-][n+]1cccc2cc(O)ccc21]

2-methyl-6-hydroxyquinoline-N-oxide:

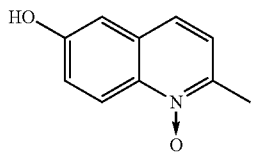

6-hydroxyquinoline:

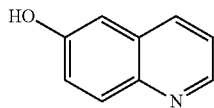

7-hydroxyquinoline:

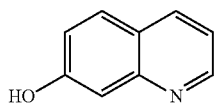

8-hydroxyquinoline:

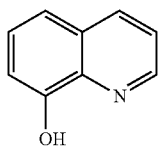

According to a preferred embodiment, the VOC volatile metabolite is chosen from p-cyanophenol, 4-nitrophenol (p-nitrophenol), m-cyano-p-nitrophenol (3-cyano-4-nitrophenol), 2,6-dichloro-4-nitrophenol, 2,6-dichloro-4-acetylphenol, thiophenol, 2,6-dichloro-4-propionylphenol, 2,6-difluoro-4-acetylphenol, 2,6-dibromo-4-acetylphenol, 1-naphthol, 2-naphthol, α-naphthylamine, β-naphthylamine, 4-nitroaniline (p-nitroaniline), umbelliferone, naphthazarin, 4-trifluoromethylumbelliferone, 4-methylumbelliferone, o-cyanophenol, m-cyanophenol, 6-cyano-2-naphthol, 6-hydroxyquinoline-N-oxide, 2-methyl-6-hydroxyquinoline-N-oxide, 6-hydroxyquinoline, 7-hydroxyquinoline, or 8-hydroxyquinoline.

Preferably, for fluorescence detection, the VOC volatile metabolite formed is chosen from umbelliferone, naphthazarine, 4-trifluoromethylumbelliferone, 4-methylumbelliferone (4-MU), a naphthol such as 2-naphthol or a naphthylamine such as β-naphthylamine.

Enzymatic Substrate

As is obvious from that which precedes, an enzymatic substrate suitable for the invention features more particularly a suitable non-volatile compound, first that can be metabolized specifically by the microorganism that is the subject of detection, and secondly, to release, precisely during its metabolization, at least one molecule of a volatile metabolite in accordance with the invention, i.e. as defined hereinabove.

Advantageously, an enzymatic substrate of the invention may be of phenol or naphthol nature, in light of the VOC metabolite considered, i.e. a phenol or naphthol derivative.

For obvious reasons, the choice of this substrate is made as a function of the enzymatic route for which characterization is sought and therefore of the targeted enzyme in the microorganism(s) for which detection is sought, such as for example a route involving glucuronidases, glucosidases, esterases, lipases, alkaline phosphatases, etc.

For example, β-D-glucuronidase activity is characteristic of the presence of coliforms, for example of *Escherichia coli* and L-alanine aminopeptidase activity allows differentiation of Gram positive and Gram negative bacteria.

Conversely, the analysis can be based on the characterization of a lack of enzymatic activity. For example, the absence of β-galactosidase activity is characteristic of *salmonella*, and the absence of peptidase activity on a substrate such as D-alanine-p-nitroaniline is characteristic of *Listeria monocytogenes* (other *Listeria* have this enzymatic activity).

Accordingly the substrate considered according to the invention may be derived from glycosidase substrates, such as α-galactosidase, β-galactosidase, α-glucosidase, β-glucosidase, cellobiosidase, β-glucuronidase, β-ribofuranosidase, hexosaminidase, α-mannosidase, 3-mannosidase, β-xylosidase, naringinase, arabinosidase, amylase, α-maltosidase and 3-maltosidase, esterase substrates, such as lipase, phosphatase and alkaline phosphatase, peptidase substrates, such as arylamidase, trypsin, dipeptidase and carboxypeptidase, deoxyribonuclease substrates, β-lactamase and nitroreductases.

This choice of substrate may also be adjusted in light of the chemical nature of the metabolite selected for the purposes of detection.

Indeed, as is obvious from that which precedes, and according to a preferred variant, the enzymatic substrate considered must lend itself to metabolization to release, via the rupture of the covalent bond embodied by the precisely metabolizable function (ester, ether, amide, etc.), at least one molecule of said VOC metabolite.

It is understood that the nature of the metabolizable function, i.e. ester, ether or even peptide, phosphoester, phosphodiester or amide, and more precisely its creation in the substrate, may impose the choice of a particular VOC metabolite. Therefore it is necessary that this metabolite lends itself to a covalent coupling of this type.

For example, p-nitrophenol, considered as a VOC volatile metabolite according to the invention, lends itself, because of its hydroxyl-OH, to a coupling with sugars (glucuronidase substrate for example), fatty acids (esterase or lipase substrate) or a phosphoric acid (phosphatase substrate).

By contrast, such a metabolite does not lend itself to a coupling with peptidase substrates. Therefore a VOC volatile metabolite having an amine —NH$_2$ must be considered, such as p-nitroaniline or 2-naphthylamine or having a thiophenol, such as for example peptidase substrates that release α-phenylthioglycine.

Selecting this VOC metabolite and the type of metabolizable function dedicated to form the substrate required according to the invention clearly falls within the skills of the person skilled in the art.

For example, peptidase substrates release α-phenylthioglycine. This decomposes spontaneously into ammonia and thiophenol. Thiophenol is then the target volatile metabolite, which may be detected, by absorbance, with a probe, 5,5'-dithio-bis-(2-nitrobenzoic acid), known as Ellman's reagent, as described in the following diagram:

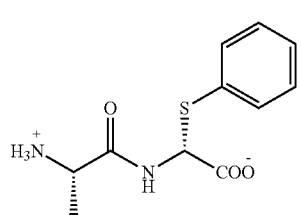
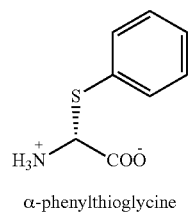
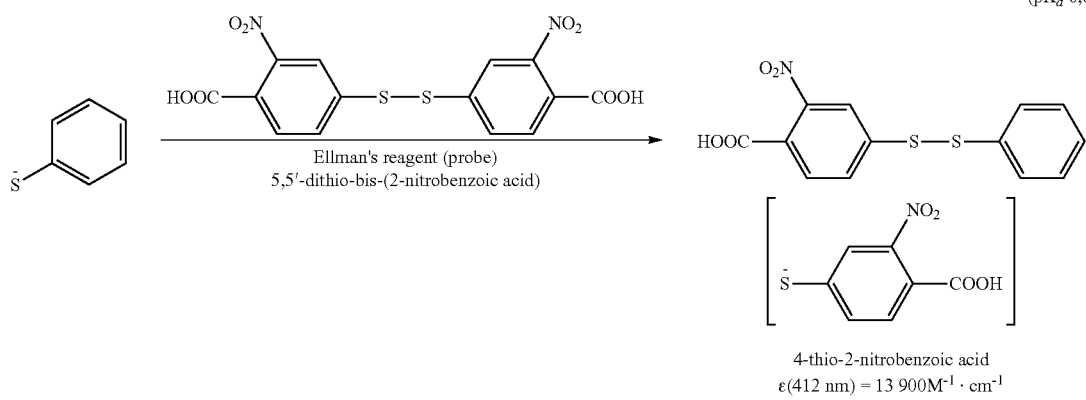
Detecting thiophenol due to the nanoporous matrix doped with Ellman's reagent shows vancomycin resistance.

As non-exhaustive examples of enzymatic substrates suitable for the invention that can release a VOC metabolite, the following compounds can be cited:

esterase substrates such as for example:

4-nitrophenyl octanoate (CAS 1956-10-1)

4-nitrophenyl myristate (CAS 146717-85-7)

4-nitrophenyl dodecanoate (CAS 1956-11-2)

β-glucuronidase substrates, such as for example 4-nitrophenyl β-D-glucuronide (CAS 10344-94-2):

β-galactosidase substrates, such as for example 4-nitrophenyl β-D-galactopyranoside (CAS 3150-24-1):

or the compound having the following formula:

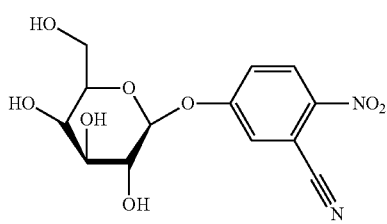

β-glucosidase substrates, such as for example 4-nitrophenyl β-D-glucopyranoside (CAS 2492-87-7):

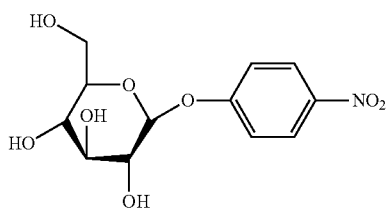

α-galactosidase substrates, such as for example 4-nitrophenyl α-D-galactopyranoside (CAS 7493-95-0):

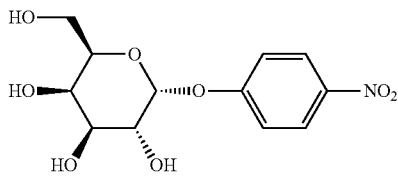 [SMILES: O=[N+]([O-])c1ccc(O[C@H]2O[C@H](CO)[C@H](O)[C@H](O)[C@H]2O)cc1]

α-glucosidase substrates, such as for example 4-nitrophenyl α-D-glucopyranoside (CAS 3767-28-0):

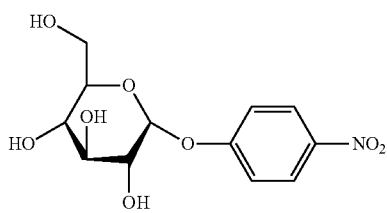

or naphthalene α-D-glucopyranoside:

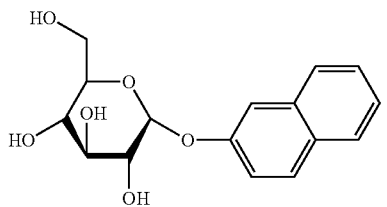

α-mannosidase substrates, such as for example 4-nitrophenyl α-D-mannopyranoside (CAS 10357-27-4):

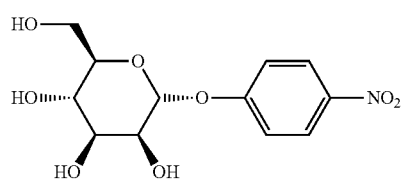

β-mannosidase substrates, such as for example 4-nitrophenyl β-D-mannopyranoside (CAS 35599-02-1):

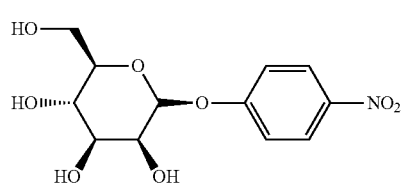

β-xylosidase substrates, such as for example 4-nitrophenyl β-D-xylopyranoside (CAS 2001-96-9):

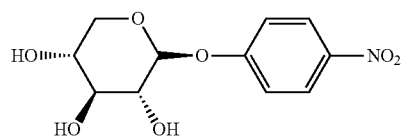

β-xylosidase substrates, such as for example 4-nitrophenyl α-L-arabinofuranoside (CAS 6892-58-6):

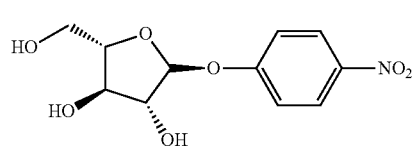

naringinase substrates, such as for example 4-nitrophenyl α-L-rhamnopyranoside (CAS 18918-31-5):

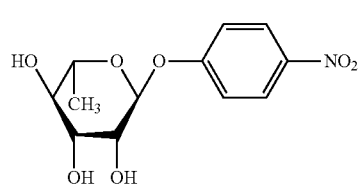

arabinosidase substrates, such as for example 4-nitrophenyl α-L-arabinopyranoside (CAS 1223-07-0):

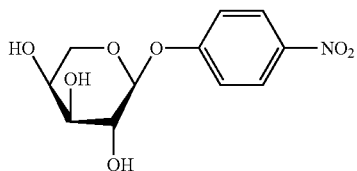

amylase substrates, such as for example 4-nitrophenyl α-L-arabinopyranoside (CAS 66068-38-0):

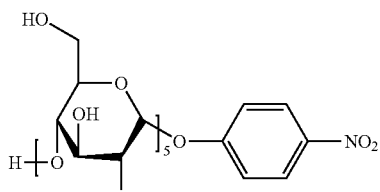

or the compound having the following formula:

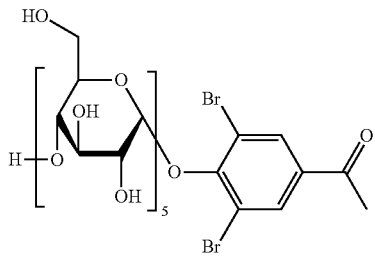

alkaline phosphatase substrates, such as for example 4-nitrophenyl phosphate disodium salt (CAS 4264-83-9):

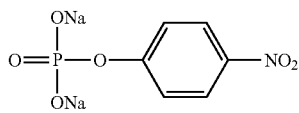

or the compound having the following formula:

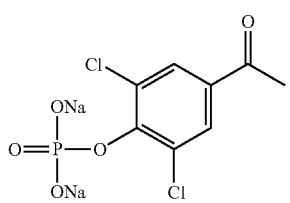

or the compound having the following formula:

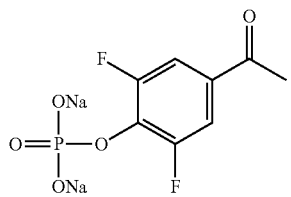

α-maltosidase substrates, such as for example 4-nitrophenyl α-D-maltopyranoside (CAS 17400-77-0):

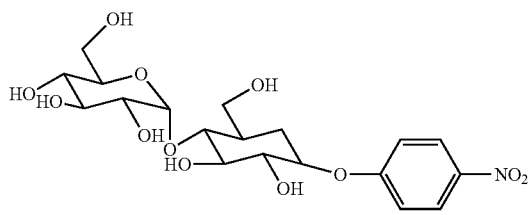 [SMILES: O=[N+]([O-])c1ccc(OC2CC(CO)C(OC3OC(CO)C(O)C(O)C3O)C(O)C2O)cc1]

β-maltosidase substrates, such as for example 4-nitrophenyl β-D-maltopyranoside (CAS 56846-39-0):

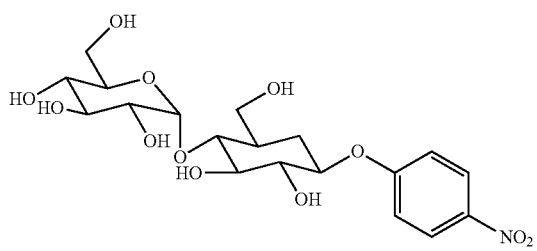 [SMILES: O=[N+]([O-])c1ccc(OC2CC(CO)C(OC3OC(CO)C(O)C(O)C3O)C(O)C2O)cc1]

or the compound having the following formula:

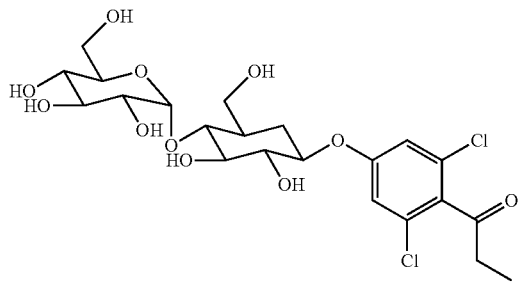 [SMILES: CCC(=O)c1c(Cl)cc(OC2CC(CO)C(OC3OC(CO)C(O)C(O)C3O)C(O)C2O)cc1Cl]

N-acetyl-β-glucosaminidase substrates, such as for example compounds having the following formula:

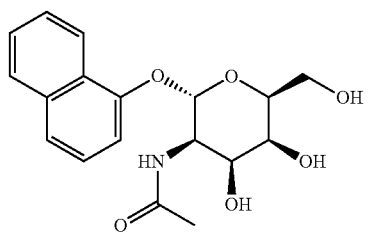 [SMILES: CC(=O)N[C@H]1[C@H](Oc2cccc3ccccc23)O[C@@H](CO)[C@@H](O)[C@H]1O]

peptidase substrates, such as for example compounds having the following formula:

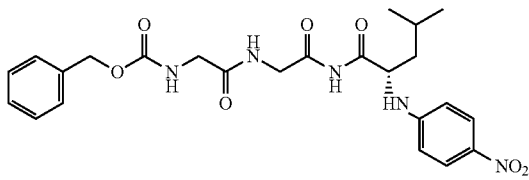 [SMILES: CC(C)C[C@H](Nc1ccc([N+](=O)[O-])cc1)C(=O)NC(=O)CNC(=O)CNC(=O)OCc1ccccc1]

trypsin substrates, such as for example compounds having the following formula:

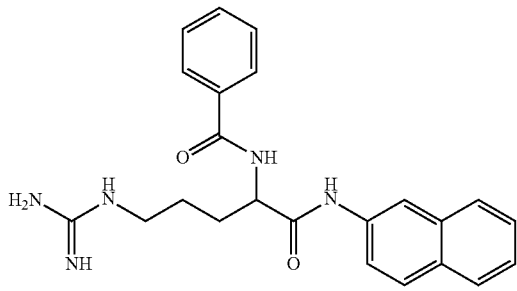 [SMILES: N=C(N)NCCCC(NC(=O)c1ccccc1)C(=O)Nc1ccc2ccccc2c1]

Preferably, the enzymatic substrates dedicated to forming the required substrates are chosen from sucrase substrates such as glucosidases, glucuronidases or galactosidases, peptidase substrates, such as arylamidases or dipeptidases such as VanX substrates and esterase substrates such as lipases and phosphatases.

As specified hereinabove this substrate considered in step 1) of the method according to the invention is used in a liquid or semi-solid phase that can contain the microorganism(s) that are the subject of detection.

According to a variant of the invention, step 2) of a method of the invention may use several distinct enzymatic substrates, metabolizable by distinct microorganisms respectively. When a method of the invention uses several distinct enzymatic substrates, they preferably generate distinct VOC metabolites during their metabolization. This embodiment is generally used to identify one or more microorganisms. Alternatively, when a method of the invention uses several distinct enzymatic substrates, these can generate the same VOC metabolite. This alternative is then used to detect one or more microorganisms.

According to another embodiment, a method of the invention may use in step 2) several enzymatic substrates generating distinct VOC metabolites that are metabolizable by a same microorganism.

Liquid or Semi-Solid Phase

The liquid or semi-solid phase considered according to the invention may be formed in whole or part of the biological medium that can contain at least one living form of said microorganism, nutritional elements necessary for proliferation of said microorganism, and an enzymatic substrate that is defined hereinabove, that can be metabolized by said microorganism into at least one VOC metabolite in accordance with the invention.

A semi-solid phase according to the invention includes in particular a structured liquid phase, for example in the form of a gel. As an example of a semi-solid phase suitable for the invention, the usual agars used for microorganism culture, such as bacteria can be cited.

The choice of nutrient elements necessary for proliferation of the microorganism clearly falls within the skills of the person skilled in the art.

As nutrient elements water, proteins, lipids, carbohydrates, vitamins, mineral elements (C, H, O, N, P, Ca, Mg, K, Na, S, etc.), oligoelements (I, Cu, Co, Cr, Mn, V, Mo, Ni, Pb, Cl, Fe, B, etc.), essential amino acids, essential acids and/or dietary fibers (cellulose, hemicellulose, etc.) can be cited.

Adding these nutrient elements clearly falls within the skills of the person skilled in the art.

What is more, many nutrient media that are specific or unspecific to the proliferation of certain microorganisms are available commercially.

Selecting the suitable medium and putting it in the presence of the biological medium to be analyzed, for the purpose of constituting the liquid or semi-solid phase that must additionally be complemented with a metabolizable enzymatic substrate, falls within routine operations of the person skilled in the art.

As explained previously, Henry's law governs the distribution of the VOC volatile metabolite between the liquid or semi-solid phase and the gas phase. It is therefore advantageous to adjust, if possible, the properties of the liquid or semi-solid phase to prefer the highest possible Henry's constant for the VOC metabolite considered.

That is, as specified previously, Henry's constant depends in particular on pH, the temperature of the liquid or semi-solid phase and the pressure of the gas phase above the liquid or semi-solid phases.

Accordingly, a feature of implementing a method of the invention may consist in the pH of the liquid or semi-solid phase being adjusted to prefer the molecular form of the VOC to one of its ionic forms.

It is particularly relevant to influence the pH of the liquid or semi-solid medium for protic compounds that dissociate measurably in water such as carboxylic acids, alcohols, phenols, thiols (aromatic or aliphatic), amines, anilines and pyridines. Only the non-dissociated molecular species can become volatile.

Accordingly, according to an embodiment, the pH of the liquid or semi-solid phase is adjusted to prefer the molecular form of the VOC to one of its ionic forms.

For example, in the case of p-nitrophenol pNP emission, the pH of the liquid or semi-solid phase will advantageously be stabilized at a value measurably less than the $pK_a$ (7.15), so that the molecular form predominates (by buffering to 6.1 with MES, 4-morpholinoethanesulfonic acid, for example).

Similarly, Henry's constant is higher when the temperature is increased. However, a temperature elevation is not generally compatible with the requirements of microbial cultures, which generally require an incubation temperature between 35 and 37° C. At a higher temperature, a drop in microbial activity is generally observed (thermal stress).

Henry's constant also depends on other parameters, in particular material transfer, the presence of surfactants, the presence of a suspended solid, the presence of a cosolvent, the salinity. It is therefore possible to adjust these parameters to obtain a high Henry's constant.

The presence of a surfactant may be prejudicial to the emission of the VOC volatile metabolite in the gas phase. It can therefore be desirable to release surfactant-type inhibitors in the culture media considered (sodium deoxycholate for example).

Accordingly, according to a preferred embodiment the liquid or semi-solid phase may comprise a reduced quantity of surfactant, or even no surfactant.

The presence of a divided solid in suspension (colloid) may also be determined to be prejudicial for the volatilization of a VOC volatile metabolite if it adsorbs on the particles, which can in particular be the case for hydrophobic VOC volatile metabolites. This is a phenomenon to take into consideration because for blood culture the media often contain colloids (activated carbon or resin) whose main role is to adsorb the antibiotics to make them inactive.

Any liquid miscible with water, such as an alcohol for example, that is present in the aqueous phase in a measurable quantity is a cosolvent. If the presence of this cosolvent increases the solubility of the VOC volatile metabolite in the aqueous phase, then it is preferable that the culture medium contains a low amount or none of it.

The water solubilities of different types of compounds (proteins, VOC volatile metabolites, surfactants, gases, etc.) can also be affected by the presence of inorganic salts. This phenomenon, called salting-out effect, has a favorable impact on Henry's constant: increased salinity in the aqueous phase accompanied by an increased constant. Consequently, provided that the presence of such a compound is not otherwise prejudicial to the development of the microorganism for which characterization is sought, it may be advantageous to consider this type of compound. Nevertheless, it is also required that the culture media generally be isotonic or almost, i.e. the equivalent of 158 mM NaCl, so as not to cause osmotic stress in the microorganisms that they contain.

According to a variant of the invention, a method according to the invention is characterized in that the matrix is arranged in the gas phase and that step 2) may use means optimizing the circulation of said VOC volatile metabolite towards the gas phase. These means may be embodied by mechanical stirring or surface nebulization of the liquid or semi-solid phase.

Accordingly, to favor material (the VOC volatile metabolite) transfer to the gas phase, the liquid phase can be stirred mechanically by magnetic bars, propellers and baffles. Nebulization aims to create a mist on the interface of the two phases, so as to maximize their contact surface area.

Particularly, in the case of a liquid phase, these optimizing means may be embodied by the liquid phase flowing on a divided inert solid phase, such as an accumulation of glass beads, to increase the surface area of the liquid-gas interface.

Consequently, and in light of that which precedes, it may be advantageous to prefer in a method according to the invention a medium with high salinity in which transfer of material will be favored due to a stirring method or a nebulization method, and in which the presence of surfactant-type inhibitors, of a divided solid in suspension and of a cosolvent increasing the solubility of the VOC volatile metabolite will be avoided.

Nanoporous Matrix

As is obvious from that which precedes, a matrix considered according to the invention is intended to interact with the metabolite that is the subject of detection if present. In other words, it has an affinity for the VOC metabolite considered.

This affinity may in particular be conditioned via an adjustment of properties of the nanoporous matrix that will be selected to be adapted to the properties of the VOC volatile metabolite emitted, in particular for its pH and/or pore size, to ensure optimal affinity and capture.

Moreover, advantageously, the nanoporous matrix may present a specific surface area of 300 to 1000 $m^2 \cdot g^{-1}$, preferably 300 to 900 $m^2 \cdot g^{-1}$, and more preferably, of 400 to 900 $m^2 \cdot g^{-1}$.

More particularly, a nanoporous matrix as required according to the invention is preferably transparent, has no intrinsic fluorescence, is inert to a probe and develops a high mass surface area.

For example, for a nanoporous matrix dedicated to capturing p-nitrophenol (pNP), basic conditions are preferred to allow deprotonation of the pNP after capture in the matrix. Accordingly, a maximum molar extinction coefficient $\epsilon_{max}$ of 18100 $M^{-1} \cdot cm^{-1}$ is obtained for phenolate pNP$^-$, whereas it is only 8300 $M^{-1} \cdot cm^{-1}$ for phenol pNP.

Similarly, the fluorescent properties of a VOC metabolite such as 4-methylumbelliferone depend on the surrounding pH (which makes it moreover a fluorescence pH probe). Therefore it is necessary to maintain the 4-methylumbelliferone adsorbed in protonation conditions that are stable.

A matrix of the invention will preferably be constituted of a solid organic or inorganic substance, dedicated to trapping the VOC metabolite formed and detecting the presence of the microorganism that is the subject of detection.

Preferably, said matrix is constituted of an organic, inorganic or hybrid organic-inorganic substance.

It is advantageously formed in whole or part of an inorganic substance or a porous organic-inorganic hybrid.

The pores will be as small as possible, to increase the specific surface area and increase the selectivity of the detector, but sufficiently large to allow the VOC volatile metabolite to pass through the nanopores.

Preferably, a nanoporous matrix suitable for the invention has a pore size distribution adjusted to the size of said VOC metabolite, and particularly below 100 nm, and preferably varying from 3 to 100 Å.

In these conditions, even when the matrix is placed in the nutrient medium, the pores form a filter, letting the volatile metabolites pass, and preferably, only the volatile metabolites. Accordingly, the matrix may be placed in the nutrient medium, or in a gas near the nutrient medium.

In a first embodiment, an organic matrix or organic-inorganic hybrid suitable to a method of the invention may be obtained from a polymer substance.

"Polymer substance" is understood to mean, in the scope of the present invention, a natural or synthetic, soluble or insoluble and in particular organic copolymer, said substance being advantageously nanoporous.

The polymer substance used in the present invention may be a hydrogel. Accordingly, the polymer substance that can be used in the scope of the present invention may be chosen from agarose; gelatin; cellulose; carboxymethylcellulose; an alginate; a polyolefin; a styrene polymer such as an advantageously porous polystyrene resin; a halogen hydrocarbon polymer such as polytetrafluoroethylene or poly(chlorotrifluoroethylene); a vinyl polymer such as a poly(vinyl decanoate) or a vinyl polyalcohol; a (meth)acrylic polymer such as poly(n-butyl acetate) or poly(benzyl methacrylate); polyethylene glycol; poly(propylene fumarate); poly(ethylene fumarate); a poly(alpha-hydroxyester); a poly(orthoester); a polyanhydride; a poly(phosphazene); a poly(ester amide); a polylactic acid; a polyglycolic acid; polycaprolacton (PCL); polydioxanone (PDO); a polyurethane; a cholesteryl anthraquinone-2-carboxylate and polymethylsiloxane gel; a 1,3:2,4-dibenzylidenesorbitol and octamethylcyclotetrasiloxane gel; a gel of an aromatic diamide with a perfluorinated chain and perfluorotributylamine in particular described in the article by Loiseau et al., 2002, Tetrahedron, vol. 58, pages 4049-4052.

It may also be a polymer of intrinsic microporosity (PIM), such as polydioxanes or polyimides, or a silicone substance, such as polysiloxanes.

In a second embodiment, a nanoporous matrix of the invention may be a nanoporous sol-gel matrix of metallic oxides and more particularly of a hybrid metallic organic-inorganic oxide, and its pore size distribution will be advantageously suited to the size of the target volatile compound.

"Nanoporous sol-gel matrix of metallic oxides" is understood to mean a nanoporous polymer network developed from at least one metallic oxide having formula (IV):

in which:
M corresponds to a metal chosen from silicon, aluminum, tungsten, titanium, zirconium, niobium, vanadium, tantalum, yttrium and cerium,
$R_a$ corresponds to a $C_1$ to $C_6$ alkyl radical or to a $C_5$ aryl,
$R_b$ corresponds to a $C_1$ to $C_6$ alkyl radical, to a $C_5$ to $C_{10}$ aryl or to a $C_3$ to $C_6$ aminoalkyl,
n, m and p are integers, such that their sum is equal to the valence of M and n is greater than or equal to 2, where m and p may be equal to 0, and
X is a halogen, preferably chlorine.

According to a preferred embodiment, the metal M of the oxide precursor of the sol-gel matrix is silicon or aluminum or zirconium. According to a preferred embodiment, the metallic oxide is $Si(OMe)_4$.

Preferably, said matrix derives from the polycondensation of alkoxysilane.

Alternatively, a matrix of the invention may derive from the polycondensation of alcoholate having formula $M(OR)_n$ and $R'M(OR)_{n-1}$ with M being chosen from Si, Al, W, Ti, Nb, Zr, Ta, and V.

Preferably, a nanoporous matrix of the invention may derive from the polycondensation of a first polyalkoxysilane that is tetramethoxysilane ($Si(OMe)_4$) and of one or more second polyalkoxysilane(s) different than the first polyalkoxysilane, in a molar ratio $Si(OMe)_4$/second polyalkoxysilane(s) of 1/0.01 to 1/1, preferably from 1/0.01 to 1/0.50, in particular from 1/0.01 to 1/0.30, particularly from 1/0.01 to 1/0.15, more particularly from 1/0.02 to 1/0.06

The sol-gel substance of the invention is porous and has pore size distribution ranging from of 3 to 100 Angströms and a specific surface area of 300 to 1000 $m^2 \cdot g^{-1}$.

The second polyalkoxysilanes used in the composition of the substance claimed may be any of the polyalkoxysilanes known in the literature, in particular the following: (N-(3-(trimethoxysilyl)propyl)ethylenediamine; 3-aminopropyltriethoxysilane; 3-aminopropyltrimethoxysilane; (3-(methylamino)propyl)trimethoxysilane; 1-(3-(trimethoxysilyl)propyl)urea; N-(3-(trimethoxysilyl)propyl)aniline; N-1-(3-(trimethoxysilyl)propyl)diethylenetriamine; bis(3-(methylamino)propyl)trimethoxysilane; diethoxydiethylsilane; diethoxydimethylsilane; diethoxy(methyl)vinylsilane; 1,3-diethoxy-1,1,3,3-tetramethyldisiloxane; dimethoxymethylvinylsilane; methyldiethoxysilane; chloro-methoxy-dimethylsilane; ethoxy(dimethyl)vinylsilane; ethoxytrimethylsilane; methoxytrimethylsilane; diethoxydiethylsilane; diethoxydimethylsilane; diethoxy(methyl)vinylsilane; 1,3-diethoxy-1,1,3,3-tetramethyldisiloxane; dimethoxydimethylsilane; dimethoxymethylvinylsilane; methyldiethoxysilane; 1,2-bis(triethoxysilyl)ethane; 1,2-bis(trimethoxysilyl)ethane; (chloromethyl)triethoxysilane; 1,3-dimethyltetramethoxydisiloxane; ethyltrimethoxysilane; triethoxy(ethyl)silane; triethoxymethylsilane; triethoxymethylsilane; triethoxy(vinyl)silane; trimethoxymethylsilane; trimethoxymethylsilane; trimethoxy(vinyl)silane; trimethoxy(vinyl)silane; tetraethoxysilane.

In particular the following can be cited: 3-aminopropyltriethoxysilane, 3-aminopropyltrimethoxysilane and even more latter.

Particularly preferred sol-gel substances are prepared essentially from tetramethoxysilane and 3-aminopropyltriethoxysilane (APTES) in a $Si(OMe)_4$/APTES molar ratio of 1/0.01 to 1/0.30, preferably from 1/0.01 to 1/0.15, more particularly from 1/0.02 to 1/0.06, most particularly from 1/0.03.

As a reminder, a sol-gel substance is a substance obtained by a sol-gel method consisting in using as precursors alcoholates having formula M(OR)n where M is a metal, in particular silicon, and R an alkyl group, and to hydrolyze them. In the presence of water, alkoxy (OR) groups are hydrolyzed, forming small particles with a size generally less than 1 nanometer. These particles aggregate and form masses that remain in suspension without precipitating, and form a sol. The increase in mass increases the viscosity of the medium, which gels. A sol-gel substance is obtained by drying the gel, by removing the solvent from the polymer network formed.

The sol-gel substance of the invention is essentially prepared from 2 to 4 polyalkoxysilanes, in particular from 2 or 3 and particularly from 2 polyalkoxysilanes. The final substance may contain from 50 to 95% of polyalkoxysilanes derivatives.

Catalysts for hydrolysis reactions and/or polycondensation of polyalkoxysilanes may be added to the starting sol. These may be an organic or inorganic acid (hydrochloric acid, sulfuric acid, nitric acid, acetic acid, tartaric acid, phthalic acid, maleic acid, etc.), an organic or inorganic base (primary amine, ammonia, sodium hydroxide, 4-amino-3-benzene-2-one, etc.) or an acid anhydride (gaseous hydrochloric acid, maleic anhydride, succinic anhydride, etc.).

This is why a sol-gel substance of the invention may further contain a catalyst for polyalkoxysilane hydrolysis reactions or a polycondensation catalyst for polyalkoxysilanes, or both. These catalysts remain in the final substance in proportions that may range from 1 to 50%.

Structuring compounds (organic polymers, neutral surfactants, anionic surfactants, cationic surfactants, etc.), that enable a regular porous structure and/or particular shape of cavity to be created, may also be added as long as they may be removed by washing or calcination without deteriorating the optical and structural properties of the matrix.

The method of preparation of a nanoporous sol-gel matrix of metallic oxides is described in more detail in application WO 2007/031657.

In a variant of the invention, a nanoporous matrix of the invention may comprise at least one probe molecule that can amplify the optical transduction signal via its interaction with said VOC metabolite trapped in said matrix. Such a probe may be a molecule that can react quickly and completely with the VOC volatile metabolite to form a more absorbent or more fluorescent compound.

"Probe molecule" is understood to mean any organic molecule having a reactive function whose reaction with a VOC metabolite causes a change of at least one of its physicochemical properties that can be detected by a suitable analytical technique, preferably a change of its spectral properties that can be detected by spectrophotometry.

The selection of a molecule probe suitable for a method according to the invention clearly falls within the skills of the person skilled in the art.

Such probe molecules are in particular described in WO 2007/031657, whose content is incorporated in the reference title. As probe molecule suitable for a method of the invention, 4-benzoylamino-2,5-diethoxybenzenediazonium chloride (Fast Blue BB) can be cited in particular for the absorbance detection of naphthol, dimethylaminocinnamaldehyde (DMACA) for absorbance detection of naphthylamine and 5,5'-dithio-bis-(2-nitrobenzoic acid), called Ellman's reagent, for absorbance detection of thiophenol.

Advantageously, the step of developing the sol-gel matrix and of incorporating at least one probe molecule, if present, will be conducted simultaneously. Indeed, the preparation conditions are generally sufficiently mild so that the probe molecules are incorporated in the sol-gel matrix without being altered.

According to another preferred embodiment, at least one probe molecule may be incorporated in the nanoporous matrix also by soaking in solution or in the vapor phase according to techniques well known to the person skilled in the art, including sublimation in particular.

Different arrangement methods, described more precisely below, may be considered for the nanoporous matrix, but in all cases it must be located in a liquid phase or in a gas phase that is adjacent to the liquid or semi-solid phase containing the microorganism to be characterized.

Optical Detection Methods for VOC Volatile Metabolites

As is obvious from that which precedes, it is the adsorption and accumulation of the VOC volatile metabolite in the pores of the matrix that will cause the change in optical properties of the nanoporous matrix and allow the presence of the corresponding microorganism to be detected.

According to a first embodiment, the detection method for the VOC metabolite is absorbance detection. The associated nanoporous matrix is then preferably transparent or absorbs poorly in the detection zone. Such a matrix does not absorb in large bands of the UV-visible spectrum. Adsorption and accumulation of a VOC volatile metabolite absorbed in the pores of the matrix will translate as increased absorbance.

In an absorbance detection method, the matrix may advantageously be in the shape of a waveguide. This increases the optical pathway without increasing the distance the VOC has to cover in the nanoporous matrix. The instrumentation may be simpler because the light is guided.

The waveguide may have a round or polygonal cross section. The waveguide may have light input and output surfaces opposite each other. It is however advantageous to have merged input and output surfaces, at one end of the waveguide, the other end being equipped with a reflective surface. This may simplify the positioning of the waveguide in the space where the VOC volatile metabolite to be detected is located, the input and output surfaces being for example turned towards a septum forming a container defining said space.

According to another embodiment, the detection method for the VOC metabolite is fluorescence detection. The associated nanoporous matrix then has no fluorescence or has low intrinsic fluorescence. Adsorption and accumulation of a fluorescent VOC volatile metabolite in the pores of the matrix will translate as increased fluorescence in the matrix.

The equipment to consider for characterizing the optical properties of the matrix may be any conventional equipment dedicated to this type of measurement.

As an illustration lamps and spectroscopes may in particular be cited.

As is obvious from that which follows, this equipment is generally arranged outside the matrix and the reservoir, but is optically coupled to the matrix. One or more optical fibers may bring the excitation signal, and also collect the transduction signal. The matrix is in the reactor, for example coupled directly by sticking to one or more optic fibers. In a variant, the light beam crosses the wall of the reactor and the nanoporous matrix.

Preferably, the matrix is coupled directly by sticking to at least one optic fiber. This device delivers better sensitivity, by removing sources of parasitic signals, for example reflections to different interfaces.

The change in the optical properties of the matrix can be followed over a range of wavelengths, in which case, a UV-visible (absorbance) spectrometer or a spectrofluorimeter are preferably used.

To follow changes in optical properties in the matrix at a given wavelength, the following can be used:
 a source, a filter, an absorbance detector, or
 a monochromatic source, a fluorescence collection system, and a detector.

DEVICE

Examples of systems for using the method according to the invention will now be described, in reference to the appended drawing.

Figure 3:
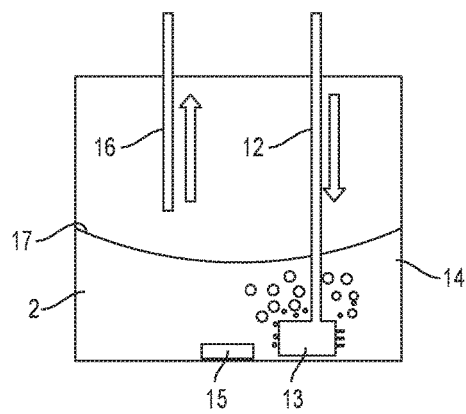
Figure 4:
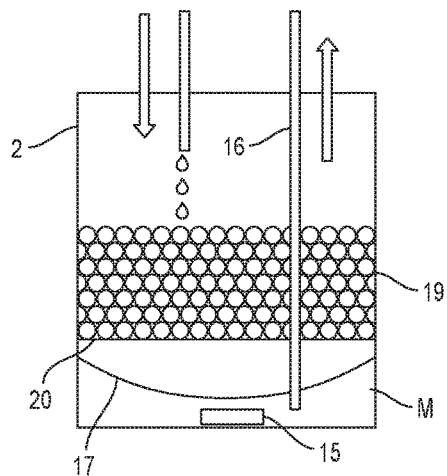
Figure 5:
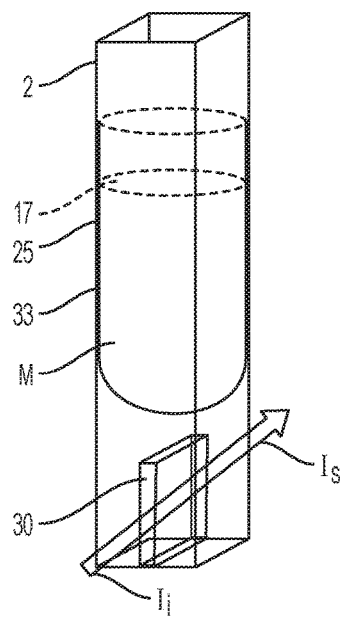
Figure 6:
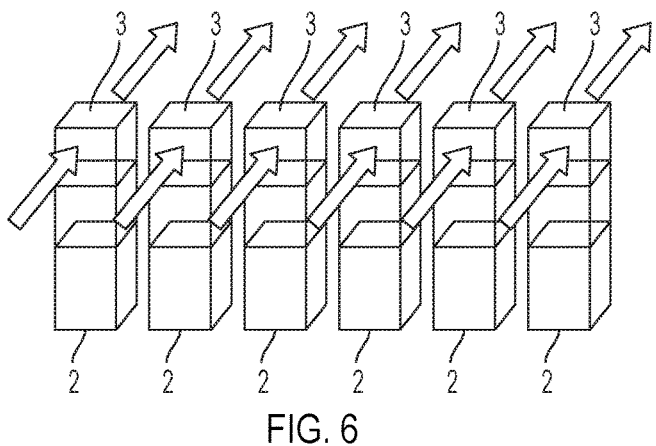
Figure 7:
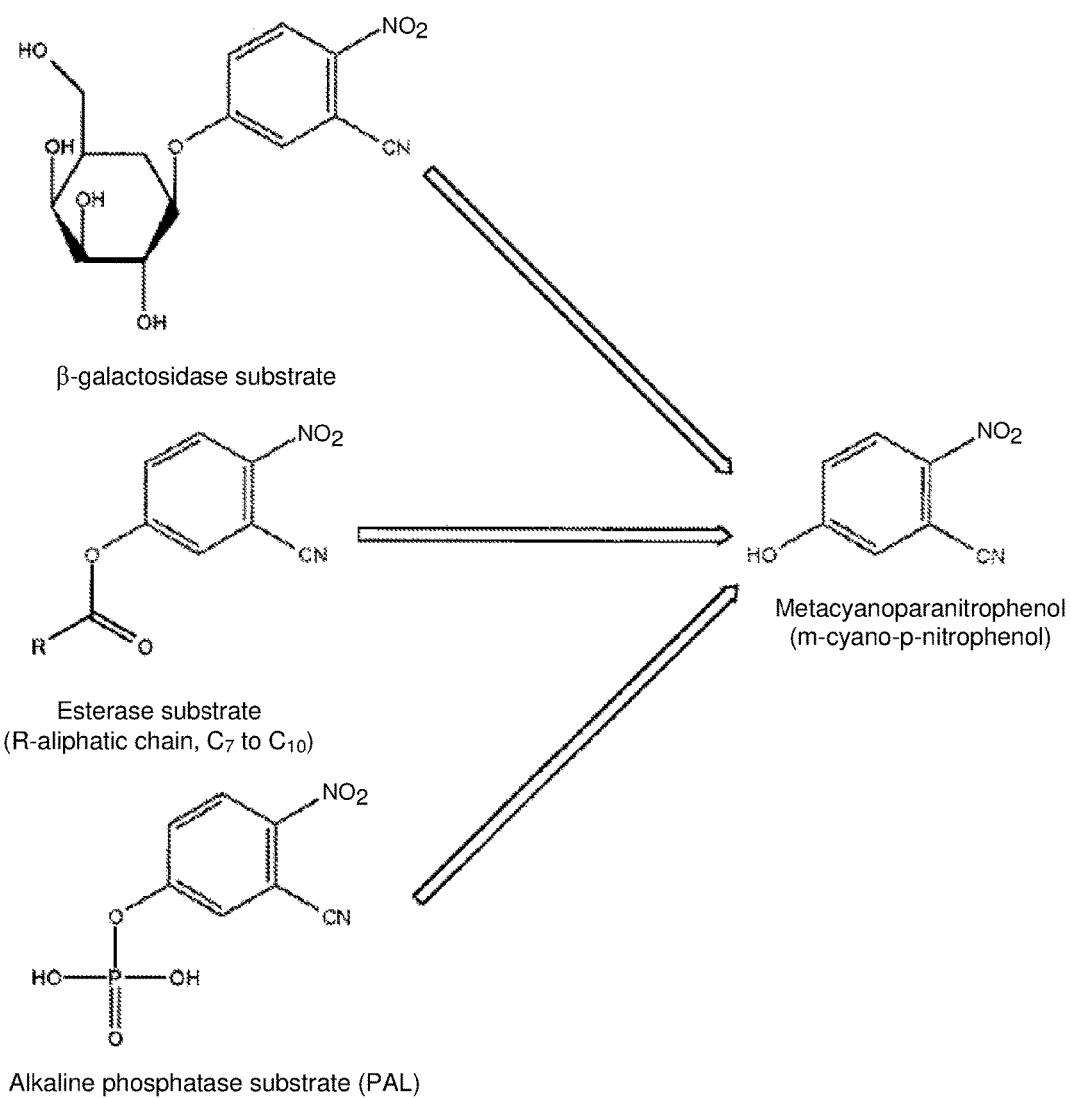
Figure 8:
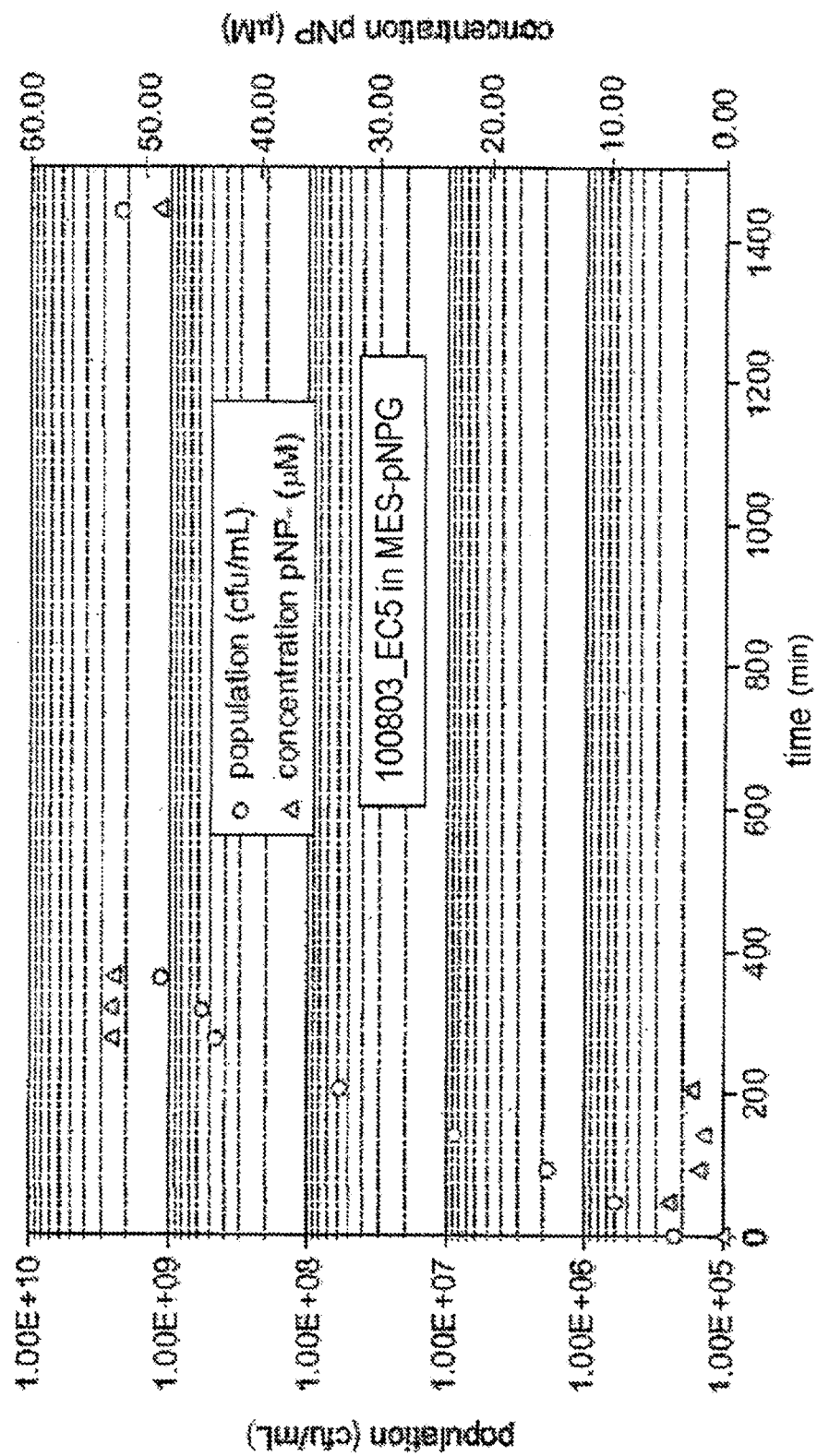
Figure 9:
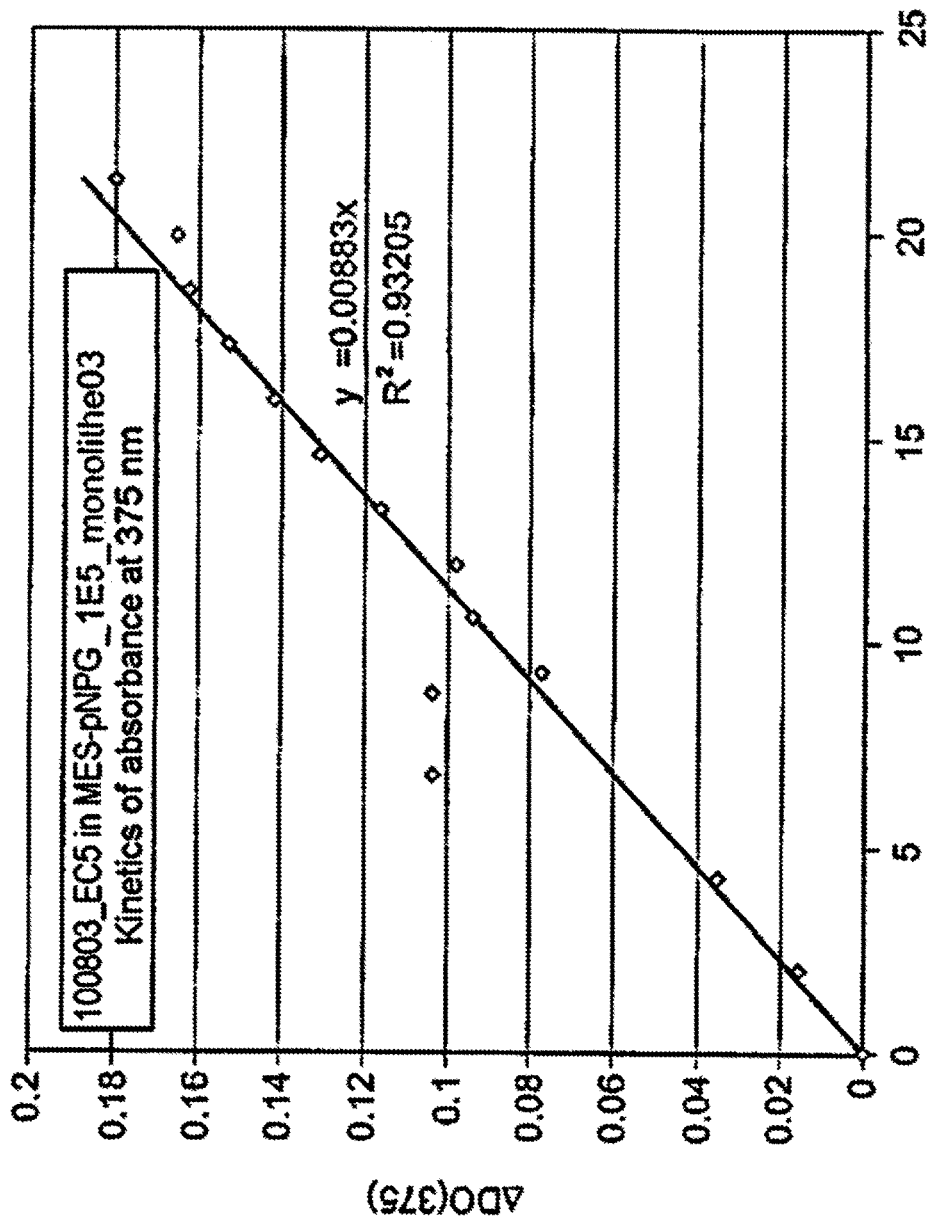
Figure 10:
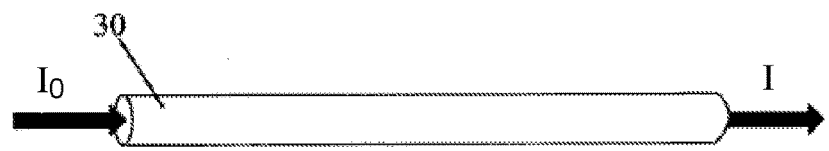
Figure 11:
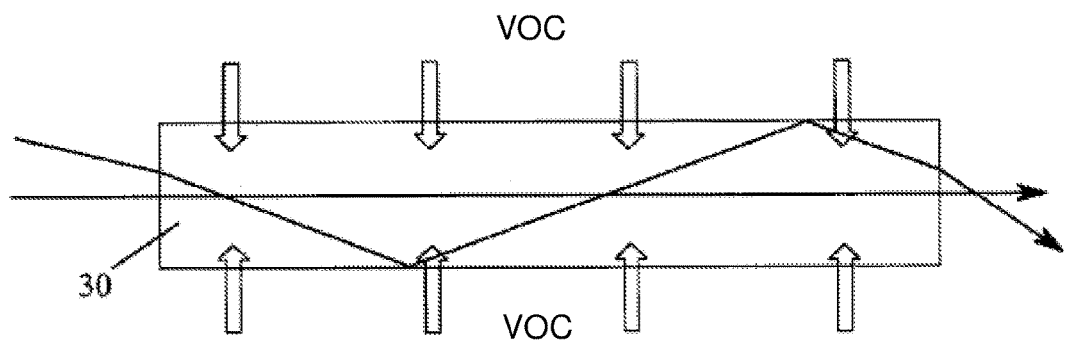
Figures 12A, 12B:
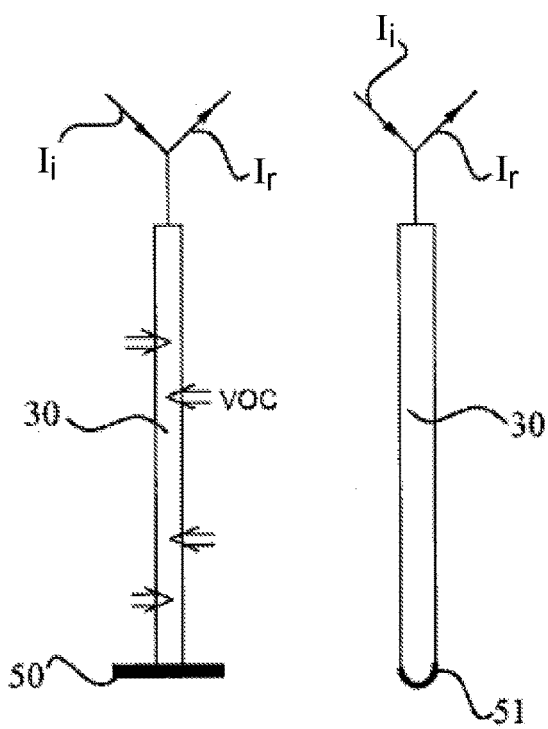
Figure 13A:
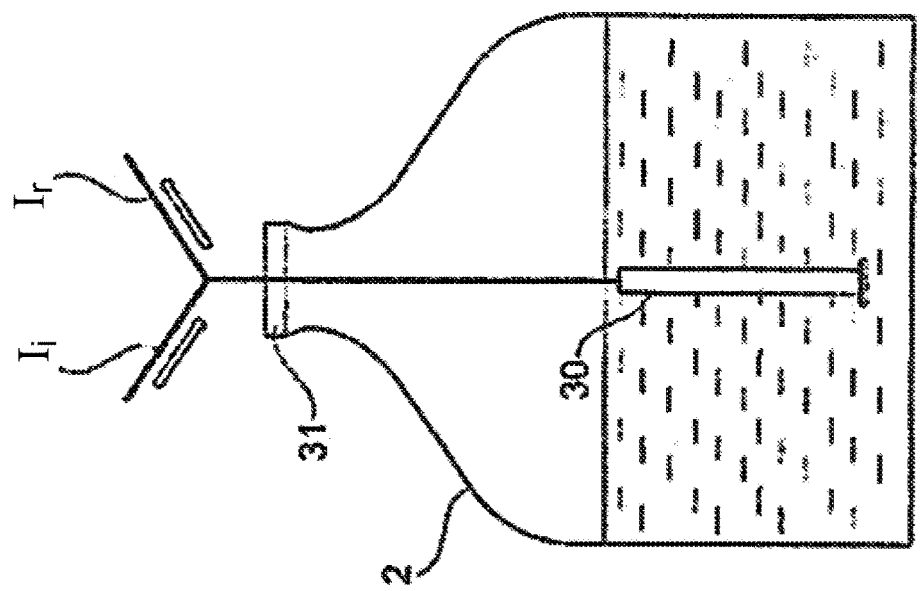
Figure 13B:
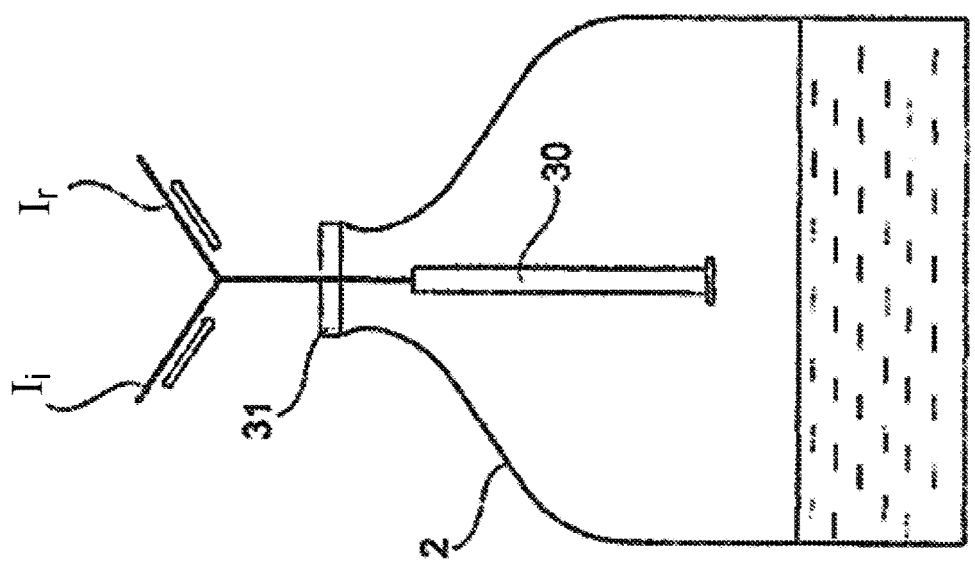

In the drawing:
 FIG. 1 represents, in a schematic and partial manner, an example of a system for using the method according to the invention,
 FIG. 2 represents, in a schematic manner, a detection system,
 FIGS. 3 and 4 represent two examples of arrangements that facilitate the extraction of gaseous metabolites of interest in the liquid or semi-solid phase of the culture medium,
 FIG. 5 is an example of an arrangement for a culture enclosure and a measuring device,
 FIG. 6 shows the possibility of using several enclosures each containing a culture medium in a given system,
 FIG. 7 represents enzymatic substrates,
 FIGS. 8 and 9 show experimental results,
 FIG. 10 represents a waveguide useful for detection,
 FIG. 11 shows the propagation of a light ray in the guide of FIG. 10,
 FIGS. 12A and 12B show other examples of detection devices,
 FIGS. 13A and 13B show the use of the detection device of FIG. 12A, in a gaseous medium and a liquid medium respectively.

System 1 according to the invention, as in FIG. 1, includes an enclosure 2, transparent and preferably without intrinsic fluorescence so as not to disturb the optical reading, containing culture medium M and, in gaseous communication with the liquid or semi-solid phase of the culture medium M, a detection device 3 that will be described in more detail below.

Detection device 3 comprises a nanoporous matrix as described previously and calls, for example, as shown, for optical detection that involves an incident light beam I whose intensity variation gives information on the presence of a VOC metabolite in the culture medium.

Figure 2:
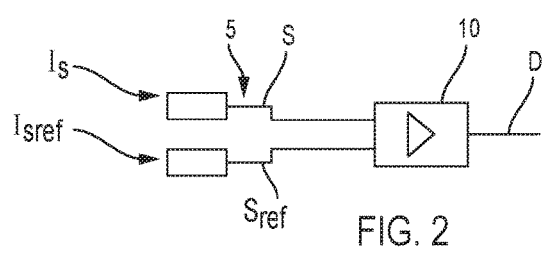

The detection may use a detection system 5, represented schematically in FIG. 2, where a signal s is compared to a reference signal $s_{rf}$ then useful information is delivered based on this comparison.

The detection uses a nanoporous matrix, as described previously, with which the VOC metabolite may come into contact and which has at least one optical property change as a function of the quantity of VOC metabolite to which the matrix has been exposed. The change in this optical property causes a change in the output light signal $I_s$, after propagation within the matrix. This output light signal may be detected by any suitable sensor, for example a photoelectric cell, which provides signal s.

The reference signal $s_{rf}$ may be the signal obtained with, for a given incident light signal $I_i$, an output light signal $I_s$ after crossing the nanoporous matrix before exposure to VOC metabolites.

Signal treatment delivered by the sensors may occur using any suitable treatment device 10, for example a computer equipped with suitable interfaces for digital-analog conversion.

The information provided by the treatment circuit 10 may be in any form, for example in the form of an alphanumeric message.

In FIG. 1, detection device 3 is shown schematically above the culture medium M, being enclosed in the same enclosure 2 that prevents gaseous exchanges with the exterior.

Any gaseous communication between the enclosure in which the culture medium is located and the enclosure in which the detection may be envisaged, for example using conduit(s) allowing gases to circulate between the liquid or semi-solid phase of the culture medium and the enclosure in which the detection occurs. Gaseous circulation may occur naturally or, as a variant be forced, for example by using a pump or a piston of any mechanism for stirring gas.

A solution to favor the extraction of VOC metabolites from the liquid phase of the culture medium may consist, as shown in FIG. 3, in bubbling the gas by bringing it into the culture medium using a conduit 12, this conduit being able to exit to a immersed diffuser 13, preferably near the base of the enclosure containing the culture medium.

The enclosure contains, preferably, as shown in FIG. 3, a mixer 15, for example with bars, that stirs the liquid phase of a culture medium.

The extraction of the gaseous medium above the enclosure may occur via the intermediate of a conduit 16 that exits above the surface 17 of the culture medium.

Another way to increase the gaseous exchange between the culture medium and the gaseous environment above the culture medium may consist in, as FIG. 4 shows, pumping the culture medium then backing up this culture medium above its surface 17, by making it flow on any element 19 suited to increasing the exchange surface area, for example arranged on a grid 20 above the surface 17 of the culture medium M.

FIG. 5 shows a variant in which a container that contains the enclosure containing the culture medium holds both this and the detection device.

The culture medium M is for example contained as shown in a tube 25, which is arranged above a nanoporous matrix 30 intended to react optically with any VOCs of interest.

The matrix is presented for example in the form of a block that is arranged to be crossed by a beam of incident light $I_i$.

Gaseous communication between the matrix 30 and the culture medium M may occur for example through a space 33 arranged between the enclosure and the wall of the container 2.

Within a system according to the invention several enclosures 2 each containing a culture medium, and each communicating with an associated detection device may advantageously be used, for example as illustrated in FIG. 6, to allow phenotype identification by putting it in the presence of a microbial strain and different enzymatic substrates all emitting the same volatile metabolite, but targeting different enzymes.

A device to count by MPN (most-probable number) and a device for AST (antibiotic susceptibility testing) can also be used.

The most-probable number (MPN) method is used to count discrete entities that are easy to detect, but difficult to count (for example bacteria in a sample of sol, blood, or in a food matrix).

The method of counting microorganisms by MPN includes the steps consisting in:

1) Taking original sample and subdividing it into sub-volumes by orders of magnitude (most often powers of 10 or 2). The microorganisms must be split into sub-volumes randomly; this therefore implies even cell distribution in the starting sample just before subdivision.

2) Testing each of the sub-volumes to determine whether the microorganism is present or absent. This step consists, in our case, in determining whether there is a non-negligible quantity, or not, of target VOC metabolite.

3) Knowing the number of sub-volumes and the results (+ or −) in each of them, Poisson's law can be used to find the most-probable value for the microorganism concentration in the original sample, and a confidence interval for the concentration measurement.

For the AST test (Antibiotic Susceptibility Testing), the steps consist in:

1) Subdividing the original sample into sub-samples of identical volumes.

2) Next incubating each of them in the presence of antibiotic. Various antibiotics are tested, generally one per antibiotic family (macrolides, beta-lactams, fluoroquinolones, etc.). Additionally, for a given antibiotic, different concentrations are tested.

3) Testing each sub-sample again to determine if there has been microbial growth or not. The result consists in revealing the antibiotics to which the tested species is sensitive, and the minimum concentration of antibiotic necessary to inhibit the growth (MIC, Minimum Inhibitory Concentration; 1 MIC value per antibiotic).

Each detection device 3, which is in gaseous communication with the corresponding culture medium, can detect whether there is degradation of the enzymatic substrate or not.

The nanoporous matrix 30 may be made in the form of a waveguide, as shown in FIGS. 10 and 11.

According to this embodiment, the nanoporous matrix preferably has a cylindrical shape, and its refractive index is greater than that of the external medium, so that it behaves as a waveguide. This matrix is illuminated by a light beam of intensity $I_0$, or incident beam. The light intensity I transmitted by the waveguide is then measured.

The interaction of the VOC produces a light absorption from the waveguide, which can be measured by comparing the incident intensity and the transmitted intensity. For example, one comparison is determining $\log(I_0/I) = e\ L\ c$ where e is the molar extinction coefficient ($Mol^{-1} \cdot l \cdot cm^{-1}$), L the optical path (cm), and c the concentration of the absorbent species created by the interaction of the VOC in the porous matrix (mol·l$^{-1}$).

$I_0$ may be determined before absorption, or by an independent measurement method, and therefore, in a general manner, by a reference measurement.

In these conditions, from the measurement for 1 (intensity of the transmitted beam) c can be estimated, since e and L are known.

A surface forming a mirror 50 can be arranged at one end of the guide, as shown in FIGS. 12A and 12B, opposite the input face through which the signal of intensity $I_0$ enters. The mirror is either flat as shown in FIG. 12A, or round as shown in FIG. 12B. This has the effect of doubling the optical pathway compared to the configuration in FIG. 10. The sensitivity of the measurement is then increased because for a given concentration c, the attenuation measured, quantified by log $I_0/I$, is higher.

In the configurations in FIGS. 12A and 12B, just like that in FIG. 10, it is the variation in the time of the return light signal that allows detection: there is no reference beam.

The reference $I_i$ denotes the incident signal and $I_r$ the return signal. In the example of FIG. 12A, the mirror 50 is for example made of silicon. In FIG. 12B, the round end 51 that reflects light is for example prepared by molding the matrix 30 in a round-based tube. The light may be reflected given the laws of refraction, due to the difference in index.

Thus, according to a preferred embodiment, optical detection is conducted after an incident beam passes back and forth in a waveguide formed by the matrix or after a waveguide formed by the matrix passes, the waveguide being for example equipped, in the case of the incident beam passing back and forth, with a mirror (50), preferably made of silicon, or of a round end (51), preferably a hemisphere.

The nanoporous matrix 30 may be arranged in the gas phase such as is shown in FIG. 13A or in the nutrient medium as shown in FIG. 13B.

In the example of FIGS. 13A and 13B, the excitation signal is brought by at least one optic fiber and the signal after crossing though the nanoporous matrix 30 is sent by at least one fiber. The fibers cross a septum 31, which seals a flask 2 defining the enclosure containing the culture medium M.

The waveguide is for example oriented vertically. The optic fiber(s) used to carry the incident and return signals are for example stuck to one end of the waveguide, for example the upper end as shown.

Preferably, the nanoporous matrix is only submerged in the liquid phase if:
a) the colored or diffusing compounds of the liquid phase do not unduly disturb the optical measurement in the matrix;
b) other solutes (pH buffers for example), that could enter into the nanopores, do not unduly disturb the optical measurement;
c) the optionally immobilized probe in the matrix does not leave the nanopores to diffuse in the liquid phase.

According to one of its features, the invention further relates to a system dedicated to the detection of a microorganism in a biological medium including an enclosure to receive a culture medium, a detection device for a VOC metabolite released by the microorganism metabolizing an enzymatic substrate, this detection system being in gaseous communication or directly in contact with said culture medium.

The enclosure containing the culture medium may have sufficiently high volume to also hold the detection system at least partially.

In an example of implementation of the invention, the culture medium is contained in a recipient that is located above a nanoporous matrix exposed to VOC metabolites, and whose optical properties are sensitive to the presence of the VOC metabolite.

This nanoporous matrix is contained in an enclosure that can be crossed by an incident light beam so that absorbance over time can be measured, as a function of the quantity of VOC metabolite having reacted with the matrix.

The nanoporous matrix may be presented in the form of a waveguide. The nanoporous matrix may be run through by a beam of incident light moving back and forth, this beam being able to reflect on a reflective, flat or concave surface. The reflective surface may be defined by a silicon mirror.

The system may include gas circulation with sampling above the culture medium and reinjection in the culture medium, preferably using a diffuser.

In another embodiment of the invention, the system includes culture medium circulation with culture medium sampling and rejection above at least one element suited to increasing the surface area of gaseous exchanges between the culture medium and the gaseous environment, preferably a bed of elements, such as beads on which the culture medium is poured.

A device in accordance with the invention may comprise:
a glass flask (non-absorbent, non-fluorescent substance);
a septum for injecting the sample into the nutrient medium;
a nutrient medium containing:
a C source
an N source
mineral salts
oligoelements
one or more enzymatic substrates
a pH buffer
optionally, adsorbents to capture residual antibiotics
optionally growth inhibitors to make the medium specific
one or more nanoporous sensors, placed in the gas phase, for the capture and optical detection of VOC volatile metabolite(s) emitted by the microorganisms.

This sensor includes, or even is constituted, by a nanoporous matrix, preferably containing silicon oxide, with a size distribution suited to the specific capture of the VOC volatile metabolite. Any porous substance created by polycondensation of alcoholates having formula $M(X)_m(OR_a)_n(R_b)_p$ may also be envisaged, in which:
M corresponds to a metal chosen from silicon, aluminum, tungsten, titanium, zirconium, niobium, vanadium, tantalum, yttrium and cerium,
$R_a$ corresponds to a $C_1$ to $C_6$ alkyl radical or to a $C_5$ aryl,
$R_b$ corresponds to a $C_1$ to $C_6$ alkyl radical, to a $C_5$ to $C_{10}$ aryl or to a $C_3$ to $C_6$ aminoalkyl,
n, m and p are integers, such that their sum is equal to the valence of M and n is greater than or equal to 2, where m and p may be equal to 0, and
X is a halogen, preferably chlorine.

The pore size is less than 100 nm, preferably varies from 3 to 100 Å. The specific surface area may vary from 300 to 1000 m$^2$/g, preferably from 300 to 900 m$^2$/g, and more preferably from 400 to 900 m$^2$/g;
a mechanical stirring device, with a bubbling or nebulization or glass bead system: any method accelerating the mass transfer of the VOC volatile metabolite from the liquid phase to the gas phase;
a membrane impermeable to liquids but not gases, to protect the sensor from liquid projections (due to the stirring);

a UV-visible absorbance spectrophotometer or a spectrofluorimeter, outside the flask.

Advantageously, steps 1) to 3) of a method of the invention may be conducted in a flask, for example a blood culture flask.

A device where different enzymes are tested on a given strain to identify a phenotype of a microorganism can also be envisaged. Different cultures containing different enzymatic substrates generating the same volatile compound are cultured with the same strain. A sensor is placed in the atmosphere of each culture to detect whether or not there is enzymatic activity. Such a device is particularly advantageous for multi-target microorganism assay.

The presence of several enzymatic substrates targeting the main enzymatic routes present in mycobacteria may advantageously allow these microorganisms to be detected in the gas phase. Two technological solutions present themselves:
  either the substrates all lead to the same VOC volatile metabolite: then a simple detection is carried out;
  or the substrates form different VOC volatile metabolites with distinct optical properties: if the number of substrates is sufficient, the mycobacteria detected can then be identified.

In the case for example of blood culture, a mixture of several enzymatic substrates targeting the most common enzymatic routes can be used, to be able to detect any of the pathogens found in blood culture.

All the pathogenic species of bacteria that can infect the blood system must present at least one of the targeted enzymatic routes.

The drawing in FIG. 7 describes the example of three enzymatic phenol substrates all emitting the same VOC volatile metabolite, m-cyano-p-nitrophenol. From mixing these 3 substrates in a culture medium 3 enzymes can be targeted: β-galactosidase, esterase and alkaline phosphatase. Therefore, any species of bacteria that presents at least one of these 3 enzymes can be detected.

In the sense of the invention, unless otherwise indicated, "one" means "at least one" and the expression "comprised between . . . and . . . " includes the limits of the interval being defined.

The examples indicated below are given to illustrate the invention, without being limiting.

EXAMPLES

Example 1

Synthesis of a Nanoporous Monolith with an Affinity for p-nitrophenol, pNP

This example shows the synthesis of a "mixed" basic Sol matrix $Si(OMe)_4$-$NH_2TEOS$. The synthetic protocol selected is the sol-gel process for a nanoporous matrix for the capture of monocyclic aromatic species, shown in application WO 2010/004225.

Starting Reagents:
Precursors:
TMOS (tetramethoxysilane) ($=Si(OMe)_4$)
APTES, $Si(C_3H_6NH_2)(OC_2H_5)_3$ ((3-aminopropyl)triethoxysilane)
Solvent:
MeOH (methanol)
Hydrolysis with ultrapure water Molar Ratios:
Alkoxides/methanol/water:1/5/4
TMOS/APTES: 0.97/0.03
Proportions for about 5 mL of 3% $NH_2TEOS$ sol
TMOS 1.786 mL
MeOH 2.43 mL
APTES 0.084 mL
Water 0.864 mL Protocol:
TMOS and MeOH are mixed with magnetic stirring for 2 min in a Pyrex beaker placed in a bath at −25° C. (ethanol and liquid nitrogen).

APTES is added to the micropipette and the whole is stirred for 2 min.

The ultrapure water is added and the whole is stirred for 30 s.

The matrices form quickly because the sol freezes quickly (1 mL in a tank, where the tanks have been pretreated at 50° C. for 24 h by degassing the oven at least three times during this period).

The tanks are closed with their stopper and left for 24 hours. The stoppers are then removed and replaced by a microporous film to let the solvents evaporate.

Example 2

β-Glucuronidase activity is targeted on two biological models, i.e. *Escherichia coli* ATCC 11775 (β-glucuronidase positive) and *Hafnia alvei* ATCC 13337 (β-glucuronidase negative).

The VOC volatile metabolite chosen is p-nitrophenol ($pK_a$=7.15).

The matrix selected is that described in example 1. It allows pNP to accumulate in pNP⁻ form.

The table below details the composition of the "MES-pNPG" culture medium that generates p-nitrophenol by β-glucuronidase activity.

This culture medium is called "MES-pNPG" because MES is its pH buffer, and pNPG (4-nitrophenyl-β-D-glucuronide) is its enzymatic substrate.

The pH is checked after calibration (3 points: 4, 7 and 10): it is equal to 6.09.

| | Component | Concentration |
|---|---|---|
| Nutrient medium (with mineral salts and trace elements) | bio-soyase | 2 g/L |
| | yeast extracts | 2 g/L |
| | NaCl | 5 g/L (86 mM) |
| | $MgSO_4$ | 250 mg/L (2.08 mM) |
| pH buffer | MES sodium salt | 16.292 g · L⁻¹ (75 mM) |
| | MES acid monohydrate | 15.994 g · L⁻¹ (75 mM) |
| β-D-glucuronidase enzymatic activity inducers | sodium glucuronate monohydrate | 108 mg · L⁻¹ (461 μM) |
| | methyl β-D-glucuronide | 55.2 mg · L⁻¹ (240 μM) |
| Enzymatic substrate of β-D-glucuronidase enzyme according to the invention | pNPG (4-nitrophenyl-β-D-glucuronide) | 35.6 mg · L⁻¹ (113 μM) |

To impose on a mainly acid form of paranitrophenol, the culture medium is buffered to $pK_a$−1, i.e. 6.15, with MES (4-morpholinoethanesulfonic acid).

2.1—Reference Control for Enzymatic Activity

The first stage is controlling enzymatic activity and bacterial growth in the liquid phase constituted by the culture medium.

The purpose is to confirm in advance, in the liquid phase, the effective formation of the VOC volatile metabolite that absorbs pNP and to quantify it (μM) by absorbance spectroscopy at 400 nm. The bacterial population is also followed (cfu/mL) over time, to determine the generation time for the bacterial model in the culture medium prepared (MES-pNPG).

The preculture is a colony of *Escherichia coli* 5 (*Escherichia coli* ATCC 11775) on a TSA plate that is suspended in 4 mL of LB culture medium (Lysogenic Broth), with stirring.

The preculture is held at 30° C. static for 14 h.

The culture is put in a LB culture medium (Lysogenic Broth), then in MES-pNPG medium as described previously.

The most concentrated preculture tube has a degree of absorbance (DO) of: DO(½x)=0.5685, i.e. an effective degree of absorbance of 1.137.

Inoculation is based on ⅕₀th for a degree of absorbance of 0.7 therefore: (1.1137/0.7)×50=81.2. Therefore inoculation is at ⅛₁st, i.e. 49 μL for a total volume of 4 mL.

Therefore 2 tubes of 4 mL of LB are inoculated at 37° C., at 250 rpm for 2 hours and 25 minutes. DO550(½x)=0.35 is measured, i.e. 0.7 effective degree of absorbance.

The buffer MES-pNPG is inoculated (t=0) to ⅟₇₀₀th: 20 μL EC5 culture in LB at 0.7 degree of absorbance for 14 mL of MES-pNPG.

The incubation is at 37° C., at 250 rpm.

For each sample:
0.5 mL is sampled for a cascade dilution in physiological serum and plated on LB agar;
1.5 mL is used to measure the bacterial concentration with DensiCheck®;
After measuring with DensiCheck®, the 1.5 mL used is filtered on Acrodisc® 0.2 μm and poured into a plastic cell for the UV-vis spectrophotometry (sweep: 200 nm/min, from 600 to 300 nm, with Milli-Q water cell for reference): the first spectrum is run;
80 μL of 5M NaOH is added to neutralize the MES buffer and turn all the pNP into phenolates anions pNP−: then a second spectrum is run (the pNP− peak will be shifted to high wavelengths so it is easier to quantify the absorbance; and the molar extinction of pNP− is higher).

The initial degree of absorbance of 0.7, which is then diluted at t=0 to ⅟₇₀₀th, corresponds to $1.54 \cdot 10^8$ cfu/mL.

The MES-pNPG buffer therefore includes $2.2 \cdot 10^5$ cfu/mL at t=0.

FIG. 8 shows growth and monitoring for β-glucuronidase enzymatic activity for a culture of *Escherichia coli* inoculated at $2 \cdot 10^5$ cfu/mL (at 37° C.) in the MES-pNPG buffer. The generation time for the exponential phase is 24 minutes.

2.2—Using the Method According to the Invention to Characterize the Presence of the Microorganism *Escherichia coli* in the Culture Medium The purpose is here to detect, in the gas phase, the VOC coming from a culture in medium MES-pNPG using a nanoporous monolith.

The device selected means absorbance of the monolith can be followed over time, between 300 and 600 nm (UVIKON 933, Double Beam UV/Vis Spectrophotometer, KONTRON Instruments) without opening the closed container in which the culture and the monolith are present together. This device is shown in FIG. 5.

The preculture is a colony of *Escherichia coli* 5 (*Escherichia coli* ATCC 11775) on a TSA plate (plate 100802_CT4 of EB) that is suspended in 4 mL of LB with ampicillin (×2 tubes), with stirring.

The preculture is held at 30° C. static for 13.5 hours.

The culture is put in LB, then in MES-pNPG buffer.

The most concentrated preculture tube has a degree of absorbance of DO(½x)=0.52, i.e. an effective DO of 1.04.

Inoculation is based on ⅕₀th for a degree of absorbance of 0.7 therefore: (1.04/0.7)×50=74. Therefore inoculation is at ⅟₇₄th, i.e. 54 μL for a total volume of 4 mL.

Therefore 2 tubes of 4 mL of LB are inoculated without ampicillin.

Incubation lasts 1.5 hours at 37° C., at 250 rpm.

A degree of absorbance of DO550(1x)=0.30 is measured (i.e. $\sim 6 \cdot 10^7$ cfu/mL).

0.5 mL is sampled for a cascade dilution to $10^{-5}$ to do a plate count: $6.2 \cdot 10^7$ cfu/mL.

The MES-pNPG buffer is inoculated at ⅟₆₀₀th: 8.5 μL of *Escherichia coli* 5 culture in LB at 0.3 of DO for 5 mL of MES-pNPG.

1.5 mL of this culture goes in the closed set-up intended for spectroscopic measurements; the rest is incubated in a classic 15 mL tube.

Bacterium *Escherichia coli* 5 is cultured in the enzymatic culture medium in a closed tube in a sealed enclosure in the presence of a basic nanoporous monolith. The absorbance kinetics of the monolith are monitored through the wall of the enclosure (a closed spectrophotometry cell). Therefore an empty cell is placed on the reference beam, to compensate for the potential absorbance of the plastic in the cell.

The incubation is at 37° C., at 150 rpm (t=0).

The monolith used is indeed transparent and colorless before the start of the experiment. The degree of absorbance of the monolith at 375 nm at t=0 is 0.25.

At t=9.25 h, the device is removed from the oven to put it in the spectrophotometerours (300 to 600 nm, data interval 1 nm, scan speed 200 nm/min; 10 cycles, cycle time 80 min (1 h20), 1 sample).

In parallel, a plate count is conducted on the tube, which contained the same inoculum and was incubated in parallel, which means the population can be estimated.

The graph in FIG. 9 shows the increase in absorbance at 375 nm of the nanoporous monolith exposed to pNP vapor (*Escherichia coli* 5 culture at 37° C. in MES-pNPG, inoculated at t=0 with $10^5$ efu/mL).

The invention claimed is:

1. A method for determining the presence or absence of at least one microorganism in a biological medium, said method comprising at least:
    providing an enclosure containing:
        a liquid or semi-solid phase formed in whole or in part of said biological medium capable of containing at least one living form of said microorganism, nutritional elements necessary for proliferation of said microorganism, and an enzymatic substrate that is specific to said microorganism and that can be metabolized into at least one Volatile Organic Compound (VOC) volatile metabolite; and
        a gas phase adjacent to said liquid or semi-solid phase, exposing at least said liquid or semi-solid phase to conditions that are favorable for said microorganism to metabolize said enzymatic substrate into at least one molecule of said VOC volatile metabolite; and
    determining, by optical transduction, the presence or absence of said VOC metabolite, an indicator of the presence of said microorganism;

wherein:
said VOC metabolite, if formed, interacts with a nanoporous matrix which has an affinity for said VOC volatile metabolite, said matrix being in a form that is separate from said enzymatic substrate and arranged in the gas phase;
the detection by optical transduction of a change in the optical properties of said matrix indicates that said matrix interacts with said metabolite; and
VOC is a metabolite specific to the metabolization of the enzymatic substrate and representative of an enzymatic route specific to the microorganism subject of detection.

2. The method of claim 1, wherein said VOC metabolite has intrinsic optical properties.

3. The method of claim 1, wherein said VOC metabolite is distinct from natural metabolites generated during microbial growth.

4. The method of claim 1, wherein said enzymatic substrate is a phenol or naphthol substrate.

5. The method of claim 1, wherein said VOC metabolite is a phenol derivative.

6. The method of claim 5, wherein said VOC metabolite is nitrophenol, cyanophenol, cyanonitrophenol, acetylphenol, a propionylphenol derivative, a thiophenol derivative, a naphthol derivative, an aniline derivative, or a naphthylamine derivative.

7. The method of claim 1, wherein said VOC metabolite is p-cyanophenol, 4-nitrophenol (p-nitrophenol), m-cyano-p-nitrophenol (3-cyano-4-nitrophenol), 2, 6-dichloro-4-nitrophenol, 2,6-dichloro-4-acetylphenol, thiophenol, 2, 6-dichloro-4-propionylphenol, 2,6-difluoro-4-acetylphenol, 2,6-dibromo-4-acetylphenol, 1-naphthol, 2-naphthol, α-naphthylamine, β-naphthylamine, 4-nitroaniline (p-nitroaniline), umbelliferone, naphthazarin, 4-trifluoromethylumbelliferone, 4-methylumbelliferone, o-cyanophenol, m-cyanophenol, 6-cyano-2-naphthol, 6-hydroxyquinoline-N-oxide, 2-methyl-6-hydroxyquinoline-N-oxide, 6-hydroxyquinoline, 7-hydroxyquinoline, or 8-hydroxyquinoline.

8. The method of claim 1, wherein the VOC metabolite is a photoacid or a photobase.

9. The method of claim 1, wherein said VOC metabolite can be detected by absorbance and/or fluorescence.

10. The method of claim 1, wherein said VOC metabolite can be detected by absorbance, and in that the associated nanoporous matrix is transparent or absorbs poorly in the detection zone.

11. The method of claim 1, wherein said VOC metabolite can be detected by fluorescence, and in that the associated nanoporous matrix is void of intrinsic fluorescence or has low intrinsic fluorescence.

12. The method of claim 1, wherein said matrix has a pore size distribution adjusted to the size of said VOC metabolite.

13. The method of claim 12, wherein said matrix has a pore size distribution below 100 nm.

14. The method of claim 1, wherein said matrix has a specific surface area varying from 300 to 1000 $m^2 \cdot g^{-1}$.

15. The method of claim 1, wherein said matrix is constituted of an organic, inorganic or organic-inorganic hybrid substance.

16. The method of claim 1, wherein said matrix derives from the polycondensation of alcoholates having formula $$M(X)_m(OR_a)_n(R_b)_p,$$

wherein:
M corresponds to silicon, aluminum, tungsten, titanium, zirconium, niobium, vanadium, tantalum, yttrium and cerium;
$R_a$ corresponds to a $C_1$ to $C_6$ alkyl radical or to a $C_5$ aryl;
$R_b$ corresponds to a $C_1$ to $C_6$ alkyl, to a $C_5$ to $C_{10}$ aryl or to a $C_3$ to $C_6$ aminoalkyl;
n, m and p are integers, such that their sum is equal to the valence of M and n is greater than or equal to 2, where m and p may be equal to 0; and
X is a halogen.

17. The method of claim 1, wherein said matrix comprises at least one probe molecule that can amplify the optical transduction signal via its interaction with said VOC metabolite trapped in said matrix.

18. The method of claim 17, wherein said probe is 4-benzoylamino-2,5-diethoxybenzenediazonium chloride (Fast Blue BB), dimethylaminocinnamaldehyde (DMACA), or 5,5'-dithio-bis-(2-nitrobenzoic acid) (Ellman's reagent).

19. The method of claim 1, wherein said matrix is arranged in the gas phase and circulation of said VOC volatile metabolite towards the gas phase is optimized.

20. The method of claim 19, wherein circulation of said VOC volatile metabolite towards the gas phase is optimized by mechanical stirring or surface nebulization of the liquid or semi-solid phase.

21. The method of claim 20, wherein circulation of said VOC volatile metabolite towards the gas phase is optimized by the liquid phase flowing on a divided inert solid phase to increase the surface area of the liquid-gas interface.

22. The method of claim 1, further defined as comprised in a method of conducting an antibiogram test (AST).

* * * * *